(12) United States Patent
Givens et al.

(10) Patent No.: US 11,305,135 B2
(45) Date of Patent: Apr. 19, 2022

(54) OXYGEN CONCENTRATING SELF-RESCUER DEVICE

(71) Applicants: Richard Givens, Humble, TX (US); Jerome A. Klein, Raymond, OH (US); David L. McDorman, Beckley, WV (US); James J. Reuther, Worthington, OH (US); Jeremy D. Seidt, Columbus, OH (US)

(72) Inventors: Richard Givens, Humble, TX (US); Jerome A. Klein, Raymond, OH (US); David L. McDorman, Beckley, WV (US); James J. Reuther, Worthington, OH (US); Jeremy D. Seidt, Columbus, OH (US)

( * ) Notice: Subject to any disclaimer, the term of this patent is extended or adjusted under 35 U.S.C. 154(b) by 476 days.

(21) Appl. No.: 16/460,168

(22) Filed: Jul. 2, 2019

(65) Prior Publication Data

US 2019/0329076 A1    Oct. 31, 2019

Related U.S. Application Data

(62) Division of application No. 15/338,369, filed on Oct. 29, 2016, now Pat. No. 10,343,000.

(Continued)

(51) Int. Cl.
*A62B 23/02* (2006.01)
*B01D 53/053* (2006.01)
(Continued)

(52) U.S. Cl.
CPC ............... *A62B 23/02* (2013.01); *A62B 7/10* (2013.01); *A62B 9/02* (2013.01); *A62B 18/02* (2013.01);
(Continued)

(58) Field of Classification Search
CPC ... A61G 7/008; A61M 16/022; A61M 16/101; A61M 2016/0027; A61M 2016/0036;
(Continued)

(56) References Cited

U.S. PATENT DOCUMENTS 3,593,711 A    7/1971  Staub, Jr. et al.
4,181,126 A    1/1980  Hendry
(Continued)

FOREIGN PATENT DOCUMENTS

WO    2012/167205 A1    12/2012

OTHER PUBLICATIONS

Notification of Transmittal of the International Search Report and the Written Opinion of the International Searching Authority for International PCT Application No. PCT/US2016/059610; European Patent Office; Rijswijk, Netherlands; dated Jan. 24, 2017.

(Continued)

*Primary Examiner* — Annette Dixon
(74) *Attorney, Agent, or Firm* — Thomas E. Lees, LLC

(57) ABSTRACT

A process for converting post-explosion gases of an inhabitable level, low-oxygen ambient environment to a breathable mixture for human consumption comprises receiving a flow of post-explosion gas with oxygen, carbon dioxide, carbon monoxide, nitrogen, and methane. The oxygen, carbon monoxide, and carbon dioxide are removed from the from the flow of post-explosion gas to create both a mixture including oxygen, carbon monoxide, and carbon dioxide; and a residual stream including nitrogen and methane. The oxygen is removed from the mixture of oxygen, carbon monoxide, and carbon dioxide, and concentrated in a primary oxygen storage canister. The nitrogen is removed from the residual stream and stored in a nitrogen storage canister separate from the oxygen storage canister. The methane is vented back to the inhabitable level, low-oxygen ambient (Continued)

environment. The stored oxygen and nitrogen are metered through a breathing mask at a habitable level of 19-21% oxygen to a user.

17 Claims, 7 Drawing Sheets

Related U.S. Application Data

(60) Provisional application No. 62/248,378, filed on Oct. 30, 2015.

(51) Int. Cl.
| | | |
|---|---|---|
| *B01D 53/54* | (2006.01) | |
| *B01D 53/62* | (2006.01) | |
| *B01D 53/75* | (2006.01) | |
| *A62B 21/00* | (2006.01) | |
| *A62B 7/10* | (2006.01) | |
| *B01D 53/22* | (2006.01) | |
| *A62B 9/02* | (2006.01) | |
| *A62B 18/02* | (2006.01) | |
| *A62B 19/00* | (2006.01) | |
| *B01D 53/047* | (2006.01) | |
| *B01D 53/14* | (2006.01) | |
| *B01D 53/86* | (2006.01) | |
| *B01J 8/00* | (2006.01) | |
| *B01J 8/02* | (2006.01) | |
| *H01M 6/38* | (2006.01) | |
| *H01M 10/0525* | (2010.01) | |
| *A62B 18/08* | (2006.01) | |
| *A61M 16/10* | (2006.01) | |
| *A61M 16/00* | (2006.01) | |

(52) U.S. Cl.
CPC .............. *A62B 19/00* (2013.01); *A62B 21/00* (2013.01); *B01D 53/0476* (2013.01); *B01D 53/1475* (2013.01); *B01D 53/1493* (2013.01); *B01D 53/22* (2013.01); *B01D 53/225* (2013.01); *B01D 53/226* (2013.01); *B01D 53/54* (2013.01); *B01D 53/62* (2013.01); *B01D 53/75* (2013.01); *B01D 53/864* (2013.01); *B01D 53/8696* (2013.01); *B01J 8/001* (2013.01); *B01J 8/0278* (2013.01); *H01M 6/385* (2013.01); *H01M 10/0525* (2013.01); *A61M 16/101* (2014.02); *A61M 2016/0027* (2013.01); *A61M 2202/0208* (2013.01); *A61M 2230/205* (2013.01); *A61M 2230/42* (2013.01); *A62B 18/08* (2013.01); *B01D 2252/30* (2013.01); *B01D 2253/20* (2013.01); *B01D 2256/10* (2013.01); *B01D 2256/12* (2013.01); *B01D 2257/502* (2013.01); *B01D 2257/504* (2013.01); *B01D 2257/7025* (2013.01); *B01D 2259/4541* (2013.01); *Y02C 20/20* (2013.01); *Y02C 20/40* (2020.08)

(58) Field of Classification Search
CPC .. A61M 2202/0007; A61M 2202/0208; A61M 2205/52; A61M 2230/005; A61M 2230/205; A61M 2230/42; A61M 2230/432; A61M 2230/65; A62B 18/02; A62B 18/08; A62B 19/00; A62B 21/00; A62B 23/02; A62B 7/10; A62B 7/14; A62B 9/02; B01D 2252/30; B01D 2253/102; B01D 2253/104; B01D 2253/106; B01D 2253/108; B01D 2253/1085; B01D 2253/20; B01D 2253/304; B01D 2256/10; B01D 2256/12; B01D 2256/245; B01D 2257/102; B01D 2257/104; B01D 2257/40; B01D 2257/502; B01D 2257/504; B01D 2257/7022; B01D 2257/7025; B01D 2257/80; B01D 2258/05; B01D 2259/40001; B01D 2259/40007; B01D 2259/40015; B01D 2259/40026; B01D 2259/40032; B01D 2259/40047; B01D 2259/40052; B01D 2259/40075; B01D 2259/40079; B01D 2259/40081; B01D 2259/402; B01D 2259/403; B01D 2259/416; B01D 2259/4541; B01D 53/0446; B01D 53/0462; B01D 53/047; B01D 53/0473; B01D 53/0476; B01D 53/053; B01D 53/1475; B01D 53/1493; B01D 53/22; B01D 53/225; B01D 53/226; B01D 53/228; B01D 53/229; B01D 53/261; B01D 53/268; B01D 53/54; B01D 53/62; B01D 53/75; B01D 53/864; B01D 53/8696; B01D 69/02; B01D 71/48; B01D 71/50; B01D 71/52; B01D 71/62; B01D 71/64; B01D 71/66; B01D 71/72; B01J 8/001; B01J 8/0278; B64D 11/00; B64D 13/00; B64D 2013/0677; B64D 25/00; B64D 37/32; C01B 13/0251; C01B 13/0259; C01B 21/0444; C01B 21/045; C01B 2210/0046; C01B 2210/0062; C08G 64/10; C08G 75/06; C08G 75/26; C08L 71/12; C10L 3/101; C10L 3/104; C10L 3/105; F25J 2200/90; F25J 2205/64; F25J 2205/72; F25J 2205/84; F25J 2215/40; F25J 2235/50; F25J 2240/02; F25J 2245/40; F25J 2245/50; F25J 2250/42; F25J 2250/50; F25J 2290/42; F25J 2290/62; F25J 2290/70; F25J 3/04169; F25J 3/04181; F25J 3/04193; F25J 3/0423; F25J 3/0429; F25J 3/04345; F25J 3/04412; F25J 3/04775; F25J 3/04866; F25J 3/04878; F25J 3/0489; F25J 3/04945; F25J 3/04963; F25J 3/04975; F25J 5/002; H01M 10/0525; H01M 6/385; Y02C 10/08; Y02C 10/10; Y02C 20/20; Y02C 20/40; Y02E 50/30; Y02E 50/346; Y02E 60/10; Y02P 20/129; Y02T 50/40; Y02T 50/44; Y02T 50/46; Y10S 62/908; Y10S 62/939; Y10S 95/903

See application file for complete search history.

(56) References Cited

U.S. PATENT DOCUMENTS

| | | | |
|---|---|---|---|
| 4,539,019 A | 9/1985 | Koch | |
| 4,681,602 A | 7/1987 | Glenn et al. | |
| 4,880,443 A | 11/1989 | Miller et al. | |
| 4,957,523 A | 9/1990 | Zarate et al. | |
| 4,963,327 A | 10/1990 | Russell | |
| 5,352,272 A * | 10/1994 | Moll ................. | B01D 53/22 96/9 |
| 5,661,987 A | 9/1997 | Zarate | |
| 6,319,305 B1 | 11/2001 | Phillips et al. | |
| 6,346,139 B1 | 2/2002 | Czabala | |
| 6,527,830 B1 | 3/2003 | Neu et al. | |
| RE43,398 E | 5/2012 | Honkonen et al. | |
| 8,211,211 B1 | 7/2012 | Knaebel | |
| 2003/0233936 A1 | 12/2003 | Crome | |

(56) References Cited

U.S. PATENT DOCUMENTS

2011/0094378 A1* 4/2011 Mitariten ............ B01D 53/229
 95/50
2013/0047988 A1 2/2013 Delp, II et al.
2013/0216627 A1 8/2013 Galbraith et al.

OTHER PUBLICATIONS

Notification Concerning Transmittal of International Preliminary Report on Patentability; for International PCT Application No. PCT/US2016/059610; The International Bureau of WIPO; Geneva, Switzerland; dated May 11, 2018.
Examination Report for European Patent Application No. 16798592; European Patent Office; Rijswijk, Netherlands; dated Apr. 17, 2020.

* cited by examiner

OXYGEN CONCENTRATING SELF-RESCUER DEVICE

CROSS REFERENCE TO RELATED APPLICATIONS

This application is a divisional application of U.S. patent application Ser. No. 15/338,369, filed Oct. 29, 2016, entitled OXYGEN CONCENTRATING SELF-RESCUER DEVICE, now allowed, which claims the benefit of U.S. Provisional Patent Application Ser. No. 62/248,378, filed Oct. 30, 2015, entitled OXYGEN CONCENTRATING SELF-RESCUER DEVICE, the disclosures of which are hereby incorporated herein by reference.

BACKGROUND

The present disclosure relates in general to emergency respiration equipment, and in particular, to self-contained self-rescuer devices.

A portable, emergency breathing system can be utilized by an individual to provide life-sustaining air when the individual is in an environment that lacks oxygen or otherwise contains toxic gases. For instance, emergency breathing systems are commonly stored in caches for access in case of an emergency retreat from a hazardous area. Portable breathing systems also find use as devices that are carried by individuals as personal protective equipment for immediate access in emergency situations. Such portable breathing systems can thus be used for timely access of life-sustaining air, e.g., if an explosion or fire occurs within a confined space (e.g., a coal mine).

BRIEF SUMMARY

According to aspects of the present disclosure, a process for converting post-explosion gases of an inhabitable level, low-oxygen ambient environment to a breathable mixture for human consumption comprises receiving a flow of post-explosion gas with oxygen, carbon dioxide, carbon monoxide, nitrogen, and methane. The oxygen, carbon monoxide, and carbon dioxide are removed from the from the flow of post-explosion gas to create both a mixture including oxygen, carbon monoxide, and carbon dioxide; and a residual stream including nitrogen and methane. The oxygen is removed from the mixture of oxygen, carbon monoxide, and carbon dioxide, and concentrated in a primary oxygen storage canister. The nitrogen is removed from the residual stream and stored in a nitrogen storage canister separate from the oxygen storage canister. The methane is vented back to the inhabitable level, low-oxygen ambient environment. The stored oxygen and nitrogen are metered through a breathing mask at a habitable level of 19-21% oxygen to a user.

According to further aspects of the present disclosure herein, a device such as a self-rescuer device comprises an intake pump, a first sieve, a second sieve, a gas processor, a primary oxygen storage canister, a nitrogen storage canister, and a breathing mask. The intake pump draws in gas, which may include toxic gas, from outside the device to create a gas stream.

The first sieve includes an input, a separated output, and a residual output. The gas stream created by the intake pump enters the first sieve through the input. Moreover, the first sieve separates the gas stream into a mixture (including oxygen), and a residual stream, whereupon the mixture flows to the separated output of the first sieve and the residual stream flows to the residual output of the first sieve. By way of example, the first sieve can separate carbon dioxide, carbon monoxide, and oxygen from the gas stream to create an oxygen, carbon dioxide, and carbon monoxide mixture that passes to the separated output. In this example, the residual stream is a carbon dioxide, carbon monoxide, and oxygen depleted stream that flows to the second sieve.

The second sieve also includes an input, a separated output and a residual output. The input of the second sieve is coupled to the residual output of the first sieve such that the residual stream flows from the first sieve to the second sieve. The second sieve separates nitrogen from the residual stream, which is output through the separated output of the second sieve. A remaining portion of the residual stream (e.g., methane gas), which is stripped of nitrogen, vents to outside of the device through the residual output of the second sieve.

The gas processer couples to the separated output of the first sieve, which separates the oxygen from the mixture. In example implementations, a chemical/physical process dissociates the oxygen from the processed gases from the first sieve. The remaining and unwanted carbon dioxide and carbon monoxide from the first stream are removed from the stream that is supplied to the user.

The primary oxygen storage canister stores the oxygen separated from the mixture until an oxygen-concentration threshold is met. The primary oxygen storage canister also releases the stored oxygen to a user of the device. Analogously, the nitrogen storage canister is coupled to the separated output of the second sieve and stores the separated nitrogen. The breathing mask receives a breathable air comprised of stored oxygen and nitrogen. Thus, as an example, habitable breathing air is released to a user of the device through a breathing mask within an exterior mask shell.

According to certain embodiments of the present disclosure, the oxygen is separated from the mixture using a third sieve. The third sieve may be an electrolytic process that separates the oxygen from the contaminated mixture by isolating and then recombining oxygen ions to form dioxygen molecules, which are stored in the oxygen storage canister. The remaining carbon dioxide and carbon monoxide mixture is vented out of the self-rescuer device.

According to other embodiments of the present disclosure, the oxygen is separated from the mixture by a catalyst bed that removes carbon monoxide from the mixture by oxidizing it into carbon dioxide. Further, the oxygen may be separated by an electrolytic sieve after the catalyst bed, a rapid-cycle amine bed after the catalyst bed, an ionic fluid bed after the catalyst bed, or a scrubbing bed after the catalyst bed.

DETAILED DESCRIPTION

According to various aspects of the present disclosure, an "oxygen concentrating self-rescuer device" is disclosed. When donned by a user, the self-rescuer device processes a gas stream (that may contain gas that is toxic, harmful, deadly, etc.) extracted from an ambient environment of the user. The self-rescuer device concentrates oxygen, which may be extracted from the environment to supply a life-sustaining, respirable gas stream to the user. In certain embodiments, the self-rescuer device separates nitrogen ($N_2$) and oxygen ($O_2$) from the ambient environment and supplies a mixture of nitrogen and oxygen, which is generally similar to normal air, to the user so the user can survive. In certain embodiments, the self-rescuer device derives oxygen from gases in the ambient environment and is thus also referred to herein as an "oxygen sieve self-rescuer device" (OSSR). Further, in certain embodiments, separated nitrogen is used to pressurize a breathing mask, so the user is not exposed to harmful gases that may be present in the environment.

For example, if an explosion occurs in a mine, the atmosphere left after the explosion may contain high (possibly lethal) levels of methane ($CH_4$), carbon dioxide ($CO_2$), and carbon monoxide (CO). At the same time, the oxygen level of the atmosphere may be perilously low (e.g., at about 8-14%). A self-rescuer device, according to aspects of the present disclosure, draws in post explosion gases from the mine (in this example), and then separates and stores nitrogen and oxygen on which the user can survive. In an illustrative implementation, once the stored oxygen is concentrated to a sufficient level for supply, the stored oxygen is mixed with the stored nitrogen, and the mixture is metered at a habitable level (e.g., 19-21% oxygen) to the user. During startup while the oxygen levels are low, an optional oxygen cache may be used to augment habitable (i.e., human life-sustaining) oxygen for the device. Accordingly, the self-rescuer device of this embodiment is implemented as a combination open loop/closed loop emergency breathing apparatus. The breathing apparatus is "open loop" in that the self-rescuer device pulls in gases from the immediate environment and processes those pulled in gases in a manner that supplies proper proportions of $N_2$ and $O_2$ to the user for respiration. The breathing apparatus is "closed loop" in that, during startup, respiration flows back and forth from the user to the self-rescuer device and is isolated from the atmosphere.

$O_2$, CO, $CO_2$, $CH_4$ Membrane Sieve/Oxygen Electrolytic Sieve OSSR

Figure 1:
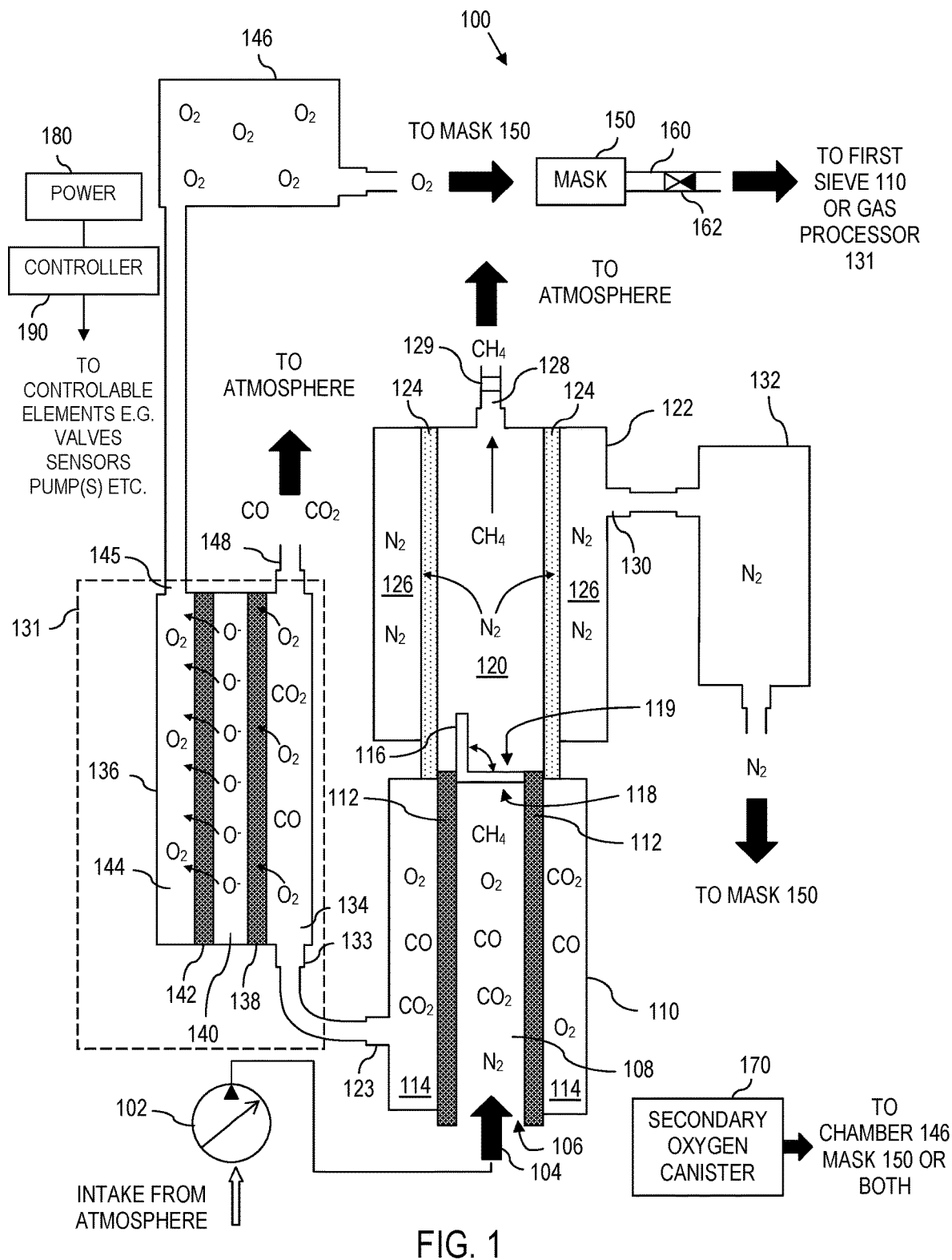
FIG. 1 is a block diagram illustrating a flow of air through an embodiment of a self-rescuer device including an electrolytic oxygen sieve, according to various aspects of the present disclosure.

Turning now to the figures, and in particular FIG. 1, a self-rescuer device 100 is illustrated according to certain aspects of the present disclosure. The self-rescuer device 100 draws in ambient gas, which may include noxious and oxygen depleted gas mixtures from the environment, into a molecular sieving apparatus.

In general, the self-rescuer device 100 comprises an intake pump, an assembly of sieves, a nitrogen storage canister, a primary oxygen storage canister, and optionally a secondary oxygen storage canister.

The nitrogen canister provides a source of nitrogen to pressurize a breathing mask of the self-rescuer device 100. The nitrogen also serves as the primary constituent of supplied respirable gas at approximately 79%, which prevents hyperoxia. The primary oxygen canister is filled by the sieving system with processed oxygen for supply to the user, e.g., by supplying the remaining 21% of the supplied respirable gas. The sieves are used in an "open loop" mode to supply habitable oxygen to the user by processing a gas stream from the ambient environment. During processing, any toxic gases separated from the gas stream are expelled back into the environment. On the other hand, the optional secondary oxygen storage canister may include any source of oxygen (e.g., a pressurized oxygen source; a solid chemical, oxygen generating source; etc.). The optional secondary oxygen storage canister is used when the self-rescuer device is operating in a "closed loop" mode to supply oxygen to the user while an "open loop" separating system is ramping up for standard operation, e.g., by concentrating oxygen from the ambient environment.

In particular, an intake pump 102 draws in gas from outside the device to create a gas stream. More particularly, the intake pump 102 includes an intake that receives gas mixtures (which may include gas that is toxic, harmful, deadly, etc.) from the ambient atmosphere and creates an intake gas stream 104 by forcing the gas mixture into a sieving system. In an example embodiment, the intake gas stream 104 may include oxygen ($O_2$), nitrogen ($N_2$), methane ($CH_4$), carbon dioxide ($CO_2$), carbon monoxide (CO), and other trace gases.

First Sieve

The intake gas stream 104 enters the sieving system and is coupled to a core 108 of a first sieve 110. The first sieve 110 includes in general, an input 106, a separated output 123, and a residual output 118. The intake gas stream 104 created by the intake pump 102 enters the first sieve 110 through the input 106. The first sieve 100 separates the gas stream into a mixture (that includes oxygen) and a residual stream. The mixture flows to the separated output 123 of the first sieve 100, whereas the residual stream flows to the residual output 118 of the first sieve 100.

More particularly, the first sieve 110 includes a membrane 112 with small pores, which divides the core 108 from an outer portion 114 of the first sieve 110. Pressure from the intake pump 102 forces smaller molecules ($O_2$, $CO_2$, and CO) through the pores of the membrane 112 to the outer portion 114 of the first sieve 110, ultimately leaving the larger molecules ($CH_4$ and $N_2$) within the core 108 of the first sieve 110. For instance, the membrane 112 may be comprised of a spaced array of fibers designed to allow smaller molecules to pass through its openings while simultaneously impeding the passage of larger gas molecules. The larger sized nitrogen molecules will be physically impeded from passing through the smaller sized openings in the fibers and will be concentrated in the through stream of the sieving apparatus. The smaller molecules of the intake gas stream 104 (i.e., $O_2$, CO, $CO_2$) will be forced through the fibers of the filter media, e.g., by pressure (Pressure Swing Absorption, Vacuum Swing Absorption, or Vacuum Pressure Swing).

After a predetermined condition is met (e.g., a certain predetermined threshold level is met, a certain pressure is met, a certain concentration of molecules is met, a certain amount of time has passed, a certain volume of gas is pumped, etc.), a cycling valve 116 opens and the residual gas (which is depleted of oxygen, carbon monoxide, and carbon dioxide) left in the core 108 is flushed as a residual stream, through a residual output 118 through a passageway into a core 120 of a second sieve 122.

However, a mixture, i.e., molecules that transition through the small pores of the membrane 112 into the outer portion 114 of the first sieve 110, do not evacuate through the residual output 118. Rather, the first sieve 110 separates carbon dioxide, carbon monoxide, and oxygen from the incoming gas stream into a mixture contained in the outer portion 114 of the first sieve 110, which flows to the separated output 123.

As illustrated, the first sieve 110 is a cylinder with the outer portion 114 completely wrapping around the core 108. However, other sieve implementations may be used. Further, the cycling valve 116 is illustrated as a hinged valve, but other valve implementations may be used.

Second Sieve

The residual stream, e.g., typically a gas mixture including nitrogen and methane molecules, enters the second sieve 122 where the nitrogen is separated from the residual gas mixture in a process that is largely analogous to that utilized by the first sieve 110. In general, the second sieve 122 comprises an input 119, a separated output 130, and a residual output 128. The input 119 of the second sieve is coupled to the residual output 118 of the first sieve such that the residual stream flows from the first sieve 110 to the second sieve 122. The second sieve 122 separates nitrogen from the residual stream, which is output through the separated output 130 of the second sieve. Also, a remaining portion of the residual stream, which is stripped of nitrogen, vents to outside of the self-rescuer device 100 through the residual output 128 of the second sieve.

More particularly, as the residual gas mixture is flushed into the second sieve 122, the nitrogen molecules pass through a membrane 124 to an outer portion 126 of the second sieve 122. (Here, the pores in the membrane 124 of the second sieve 122 are relatively larger than the pores in the membrane 112 of the first sieve 110.) The nitrogen collected in the outer portion 126 of the second sieve 122 passes through a separated output 130 and collects in a nitrogen storage canister 132.

On the other hand, the residual gas mixture (now oxygen-depleted, carbon monoxide-depleted, carbon dioxide-depleted, and nitrogen-depleted) vents from the self-rescuer device 100 through a residual output 128 (e.g., an opening) in the core 120 of the second sieve 122. In some embodiments, the opening (i.e., via the residual output 128) includes an optional valve 129 that prevents the residual gas mixture from escaping the second sieve 122 until a predetermined condition is met (e.g., a certain predetermined threshold level is met, a certain pressure is met, a certain concentration of nitrogen is met, a certain amount of time has passed, etc.).

Nitrogen Storage Canister

The nitrogen collected into the nitrogen storage canister 132 may be used to pressurize a breathing mask. In some embodiments, the self-rescuer device 100 includes nitrogen-purity sensors, and if the purity of the nitrogen to the nitrogen storage canister 132 is below a predetermined threshold, control electronics recirculate the nitrogen to the first or second sieve 110, 122 for further filtration before allowing the nitrogen into the nitrogen storage canister 132. If the nitrogen purity levels are above the predetermined threshold, then the nitrogen is allowed into the nitrogen storage canister 132. The nitrogen collected into the nitrogen storage canister 132 is also utilized by a corresponding breathing mask to provide a respirable gas to the user.

Gas Processor

A gas processor 131 couples to the separated output 123 of the first sieve 110. Essentially, the gas processor 131 separates oxygen from the mixture contained in the first sieve 110. For instance, in an example embodiment, the oxygen, carbon monoxide, and carbon dioxide mixture collected in the outer portion 114 of the first sieve 110 flows from the separated output 123 into the gas processor 131, which is implemented as a third sieve 136. The third sieve 136 comprises in general, an input 133, a separated output 145, and a flow output 148.

The input 133 of the third sieve 136 is coupled to the separated output 123 of the first sieve 110 to receive flow therefrom.

The third sieve 136 separates oxygen from the flow therein. The separated oxygen of the third sieve 136 is coupled to a primary oxygen storage canister 146 described more fully herein. On the other hand, the flow output 148 of the third sieve 136 vents the oxygen-stripped flow out of the self-rescuer device 100.

More precisely, as shown, the mixture flows from the separated output 123 of the first sieve 110 to the input 133 of the gas processor 131 (third sieve 136 in this example embodiment) and enters a first chamber 134 thereof. Notably, $CO_2$ is classified as an asphyxiant. The effects of $CO_2$ (shortness of breath, increased heart rate, confusion and headache) can manifest at 5% (50,000 parts-per-million (ppm)) concentrations. $CO_2$ is toxic at 7% to 10% (70,000 ppm to 100,000 ppm) concentrations causing muscle tremors, sweating, and unconsciousness. In contrast, CO concentrations of as little as 0.04% (400 ppm) can produce frontal headaches and confusion, and CO concentrations of approximately 1% (10,000 ppm) produce convulsions, unconsciousness, and rapid death. As such, the electrolytic sieve 136 filters out the CO and $CO_2$ molecules from the $O_2$ molecules.

The oxygen molecules pass through a membrane 138 as oxygen ions ($O^-$) to a second chamber 140 of the third sieve 136. The oxygen ions are recombined to form dioxygen molecules ($O_2$) by passing through a catalyst coating on a second membrane 142 to a third chamber 144 of the third sieve 136. The collected dioxygen molecules flow out the output 145 of the third sieve 136 and are concentrated and stored in the primary oxygen storage canister 146, as noted above.

In this regard, the third sieve 136 defines an electrolytic sieve 136 that separates the oxygen by separating oxygen ions and combining the oxygen ions to form dioxygen molecules, which are stored in the primary oxygen storage canister 146.

In certain embodiments, the carbon monoxide molecules and carbon dioxide molecules remain in the first chamber 134 as the electrolytic sieve 136 only allows the oxygen to pass through into the next chamber 140. Thus, the carbon monoxide molecules and carbon dioxide molecules do not pass through the first membrane 138 and remain in this chamber 134 until vented out of the self-rescuer device 100 through the flow output 148 of the electrolytic sieve 136.

Primary Oxygen Storage Canister

In an example embodiment, the primary oxygen storage canister 146 stores the oxygen separated from the mixture until an oxygen-concentration threshold is met, as will be described in greater detail below.

The concentrated oxygen stored in the primary oxygen storage canister 146 can be used to supply life-sustaining oxygen to the user of the self-rescuer device 100. In some embodiments, an oxygen-purity sensor (not shown) senses the purity of the oxygen in the primary oxygen storage canister 146 (or before the processed gas reaches the primary oxygen storage canister 146). If the oxygen purity is above a predetermined threshold, then the oxygen may be released to the user. However, if the oxygen purity is below the predetermined threshold, then the still toxic gas may be looped back to an upstream component of the self-rescuer device 100 for further sieving. For example, the gas mix may loop back to an insertion point located before the electrolytic sieve 136 or before the first sieve 110.

Breathing Mask

As schematically illustrated, a breathing mask 150 receives oxygen stored in the primary oxygen storage canister 146 for use by a corresponding breathing mask 150. Also, as schematically illustrated, the breathing mask 150 receives nitrogen from the nitrogen storage canister 132. In this manner, the breathing mask 150 receives a breathable air comprised of stored oxygen and nitrogen. As such, the self-rescuer device 100 draws in a gas stream, and therefrom, separates, processes, and concentrates habitable gases directly from the atmosphere, e.g., which may include a post explosion atmosphere, fire atmosphere, other toxic or hazardous environment, or combinations thereof.

Loop-Back

In some embodiments, the self-rescuer device 100 includes a loop-back channel that takes the air exhaled by the user and runs it through the self-rescuer device 100. In an example implementation, as schematically illustrated, a loop-back channel 160 extends from the breathing mask 150 to an input of the self-rescuer device 100, e.g., right before the gas processor 131 (e.g., electrolytic sieve 136) or the first sieve 110 to recycle exhaled oxygen back into the self-rescuer device. That way, the self-rescuer device 100 may recover the oxygen exhaled by the user. In certain embodiments, the loop-back channel 160 includes a check valve 162 to prevent gases from getting to the user through the loop-back channel 160. That is, the check valve 162 can prevent flow from the at least one of the first sieve and the gas processor from entering the breathing mask via the loop-back channel.

Sensors

Various embodiments include flow sensors and pressure sensors (described more fully with reference to FIG. 6) that determine how much oxygen the user requires. Control electronics, including a controller uses this sensor feedback to supply a mix of oxygen and nitrogen to the user to match the immediate needs of the user. For example, if a user experiences heavy physical exertion, then the user's breathing may become quicker and deeper, and the self-rescuer device senses a flow/pressure increase. Thus, the self-rescuer device 100 comprises a pressure sensor and a control sensor to ensure that oxygen within breathable portions of the breathing mask is approximately 21% oxygen, despite the user's breathing pattern. In an example embodiment, control electronics then increase the flow of oxygen (or mix of oxygen and nitrogen) to the user. Conversely, at times when the user does not require as much respirable gas, the controller decreases the air flow. Thus, the user can maintain breathing 21% oxygenated air no matter the exertion level of the user. Such a variable flow rate helps conserve power resources of the self-rescuer device 100. To aid in the variable flow, some embodiments include a variable-flow pump coupled to a sensor. An example variable-flow pump is described in greater detail in reference to FIG. 2.

Power

Power 180 may be supplied to the self-rescuer device 100 in any desirable fashion. For example, the self-rescuer device 100 may employ batteries, thermal generators, trickle chargers, combinations thereof, etc. If a battery is used, anode and cathode sections of the battery may be kept isolated until activation of the self-rescuer device. As such, the battery will not leak current that otherwise may occur during long periods of storage (e.g., until the self-rescuer device is to be used in emergency situations). In several embodiments, the self-rescuer device includes more conventional high-storage capacity batteries (e.g., lithium-ion batteries). In such a case, a charge indicator can alert a user to the charge capacity and charge left on the battery.

In systems requiring a charger, a trickle charger may be used. The trickle charger charges the battery at a rate equal to its discharge rate, so the battery will always be at full charge while attached to the trickle charger. In turn, the trickle charger can receive power from any available power source (e.g., mine trolley, phone lines, etc.).

In some embodiments, the self-rescuer device 100 includes thermal generators that convert some thermal energy into electricity. As an example, heat produced by the electrolytic sieve may be converted to electricity.

In some embodiments, the power 180 can be utilized to power a controller 190 forming part of corresponding control electronics, which in turn, can be used to power valves, sensors, pump(s) and other controllable elements.

Miscellaneous

Figure 6:
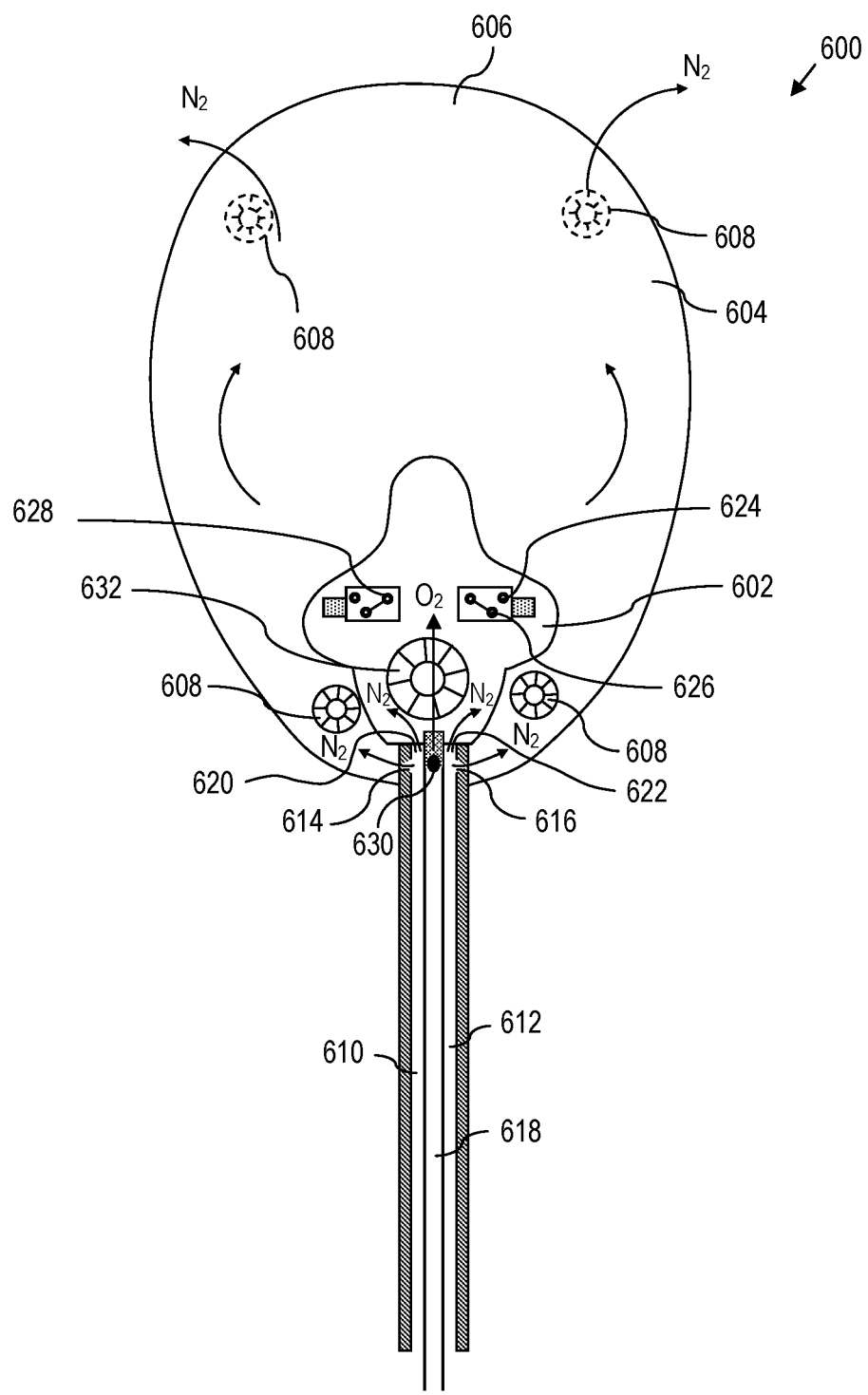
FIG. 6 is a diagram illustrating a self-rescuer device that may be used with any of the embodiments of the self-rescuer device, according to various aspects of the present disclosure.

The separate nitrogen storage canister 132 and primary oxygen storage canister 146, allow for the flows of the canisters to be regulated separately. Therefore, the nitrogen can be used to pressurize the breathing mask (FIG. 6). In this way, only the nitrogen is used to pressurize the breathing mask, so the self-rescuer device 100 does not waste precious oxygen in the pressurization process. The pressurization also allows for natural breathing when donning the system. Moreover, the nitrogen and oxygen can be mixed, e.g., at a 79:21 ratio of nitrogen-to-oxygen to supply a breathable air to the user. The concentration performed by the self-rescuer device 100 provides an advantage over other types of self-rescuer devices that require nascent life-sustaining amounts of oxygen in the atmosphere and process or catalyze specific toxic gases into less lethal gases (such as catalyzing carbon monoxide into carbon dioxide).

Some embodiments include a secondary oxygen storage canister 170 (i.e., an optional oxygen supply cache). The optional secondary oxygen storage canister 170 can be used, for instance, while the self-rescuer device 100 is concentrating oxygen initially during startup, while the oxygen in the primary oxygen storage canister is below the oxygen-purity threshold, when the oxygen levels are otherwise too low or when there is not enough oxygen to meet the immediate and urgent demands of the user. The secondary oxygen storage canister supplies oxygen to the primary oxygen storage canister 146, the breathing mask 150 (and thus to the user), or both. Thus, the secondary oxygen storage canister 170 can supply oxygen on an as-needed basis. Examples of the secondary oxygen storage canister 170 include, but are not limited to: an oxygen bottle, solid oxygen-generating chemicals, etc.

In an example implementation, the electrolytic oxygen sieve can experience a startup delay lag. As such, a small cache of compressed oxygen or solid oxygen generating chemicals, e.g., from the secondary oxygen canister 170, is used to supply oxygen initially until the $O_2$ sieving subsystem comes up to full operation. After the $O_2$ sieving subsystem comes on line, the additional mass/volume of the startup $O_2$ module from the secondary oxygen canister 170 can be disconnected from the self-rescuer device 100 and discarded.

The self-rescuer device 100 concentrates and stores oxygen without depleting resources within the self-rescuer device 100. Within the embodiment of FIG. 1, the self-rescuer device 100 can provide oxygen to a user even where the outside atmosphere does not have breathable levels of oxygen. Notably, respirable gas is generated without relying on an oxygen-producing cache as the sole or otherwise long-term source of oxygen (the oxygen supply cache of the present disclosure is optional in the self-rescuer device 100 and is only used to carry over the startup of the sieve system). As such, the self-rescuer device 100 can supply oxygen to a user as long as there is power to the self-rescuer device 100. This is an advantage over other self-rescuer devices that require chemicals that deplete when used to provide the oxygen to a user.

Further, the intake pump 102 may activate before the user dons the self-rescuer device 100. As such, the user may have available oxygen by the time the user dons the self-rescuer device 100.

Also, the user does not need to forcibly breathe to filter the ambient gases or concentrate the oxygen, which allows the user to breathe normally through the self-rescuer device 100. The positive pressure inside the breathing mask eliminates any resistance to inhalation and may assist the breathing for users with compromised lung capacity and respiratory conditions (e.g., black lung, emphysema, heavy smokers, etc.). On the other hand, conventional mask devices require the user to forcibly breathe into the conventional device for proper operation and can compromise the ability of users with lung conditions to effectively use these systems.

While the first sieve 110 is described and illustrated as being a separating sieve (i.e., membrane separation), the first sieve 110 may be any type of sieve. For example, the first sieve 110 may be an adsorption/desorption sieve or an absorption/desorption sieve. In these types of sieves, a first cycle pressurizes the sieve so smaller molecules (e.g., $O_2$, $CO_2$, and CO) in the gas mixture are forced within (absorption) or onto a surface (adsorption) of a cell with small pores, while larger molecules flow out of the first sieve 100. In the second cycle, the pressure is removed (or a vacuum is applied) and the absorbed/adsorbed molecules flow out of the sieve. For example, the first sieve 100 may use pressure-swing adsorption, vacuum-swing adsorption, or vacuum-pressure-swing adsorption.

Further, the second sieve 122 may be any of the types of sieve described in reference to the first sieve 110. Also, the first sieve 110 does not necessarily need to be the same type of sieve as the second sieve 122.

The self-rescuer device 100 is not adversely affected by chemical storage, like compressed gas or solid chemical oxygen stores that are limited in gas quantity and negatively impact the operational duration of current rescue breathing technologies. Rather, the self-rescuer device 100 concentrates and purifies on demand, the $N_2$ and $O_2$ that is required for habitable air from the ambient atmosphere, e.g., greater mine or enclosed space volume, and is virtually unlimited in this aspect. The usable duration of the self-rescuer 100 is only limited by the battery power required to keep aspects of the self-rescuer operational. It is anticipated that battery stores will be sufficient to minimally double the effective operational time of current technologies.

It should be understood that the embodiment of FIG. 1 may also and/or alternatively include other features described more fully herein with regard to the remaining figures unless otherwise noted.

$O_2$, $CO_2$, CO Membrane Sieve/CO Catalyzing/$CO_2$ Scrubbing OSSR

Figure 2:
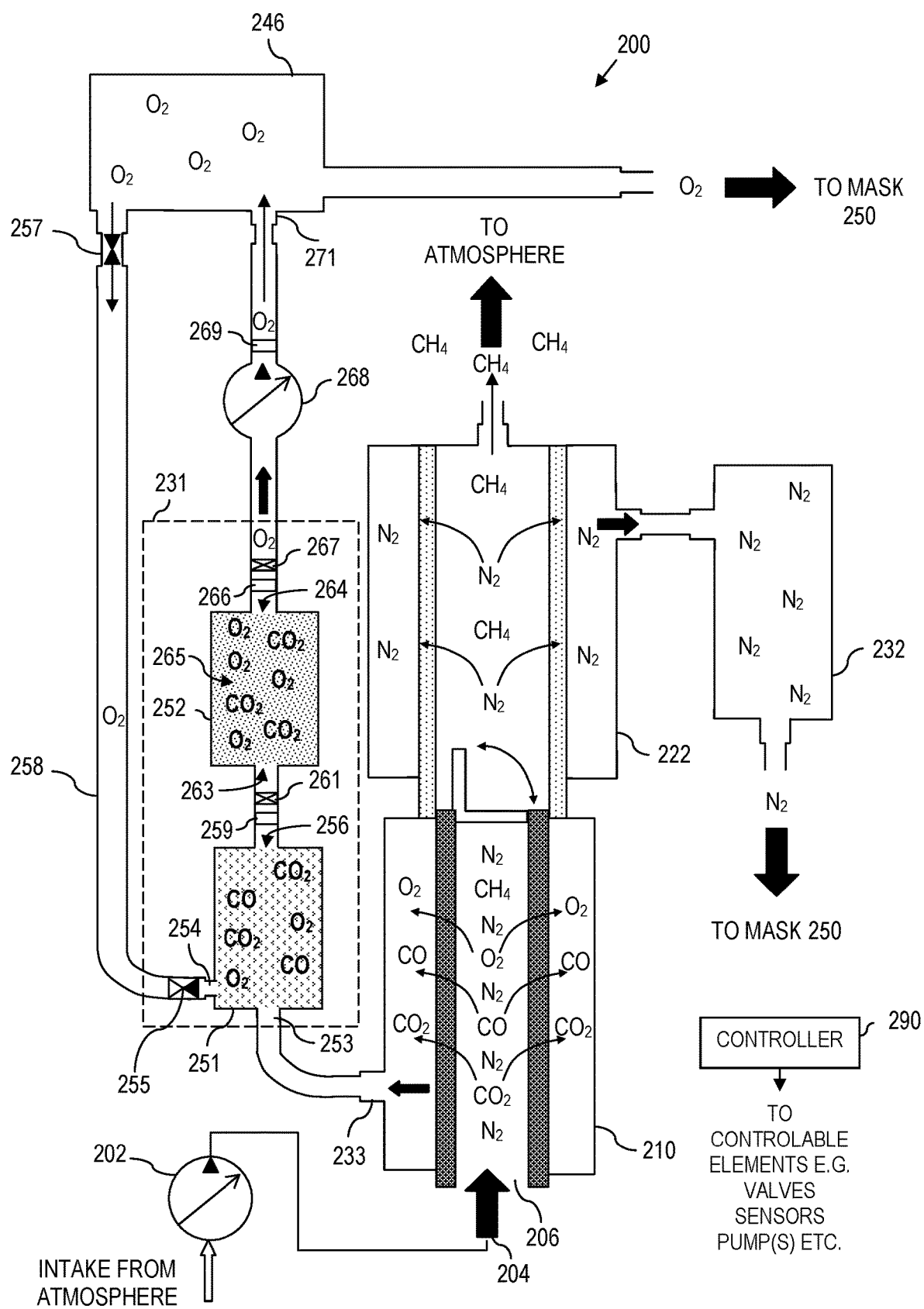
FIG. 2 is a block diagram illustrating a flow of air through another embodiment of a self-rescuer device including a catalyst bed and a scrubbing bed, according to various aspects of the present disclosure.

Turning now to FIG. 2, a self-rescuer device 200 is illustrated according to further aspects of the present disclosure. In this implementation, elements of the self-rescuer device 200 are analogous to like elements of the self-rescuer device 100 of FIG. 1 and are thus indicated with reference numbers 100 higher in FIG. 2, then their counterpart in FIG. 1. Notably, features and elements from other embodiments can be included in the embodiment of FIG. 2, unless otherwise noted. Likewise, the features and elements of FIG. 2 can be shared with the other embodiments herein unless otherwise noted. For sake of clarity of discussion, certain optional components schematically shown in FIG. 1 are omitted in FIG. 2. However, in general, all components described throughout this disclosure can be included in the embodiment of FIG. 2 unless otherwise noted.

The self-rescuer device 200 features an oxygen, carbon monoxide, carbon dioxide sieve subsystem like that of the first embodiment. However, the self-rescuer device 200 includes an oxygen concentrating/purifying subsystem that does not sieve oxygen directly out of the ambient environment. Rather, the self-rescuer device 200 concentrates and purifies oxygen by integrating catalyst and scrubbing components. These chemical compounds remove the unwanted gases from this gas feed stream.

The self-rescuer device 200 includes an intake pump 202, a first sieve 210, second sieve 222, nitrogen storage canister 232, and oxygen storage canister 246 as illustrated. The intake pump 202, first sieve 210, second sieve 222, nitrogen storage canister 232, and oxygen storage canister 246 operate similarly to their respective components 102, 110, 122, 132, 146 of the self-rescuer device 100 of FIG. 1 and the other embodiments discussed herein. However, instead of an electrolytic sieve (136, FIG. 1), the gas processor 231 of the self-rescuer device 200 comprises a catalyst bed 251 and an optional scrubbing bed 252.

The catalyst bed 251 comprises a flow input 253, an oxygen input 254, a check valve 255, and an output 256. Notably, the catalyst bed 251 catalyzes carbon monoxide molecules to form carbon dioxide molecules. In this regard, the flow input 253 is coupled to the separated output 223 of the first sieve 210. The oxygen input 254 is coupled to the primary oxygen storage canister 246 and the check valve 255 ensures that oxygen from the primary oxygen storage canister 246 can enter the catalyst bed 251 but contents from the catalyst bed 251 cannot enter the primary oxygen storage tank 246 through the oxygen input 254. The output 256 is coupled to the primary oxygen storage canister 246 (e.g., either directly such as where there is no scrubbing bed 252, or indirectly, e.g., via the scrubbing bed 252).

More particularly, the catalyst bed 251 includes a catalyst that accelerates oxidization of carbon monoxide into carbon dioxide using the oxygen in the gas mixture. If more oxygen is needed to oxidize the carbon monoxide, then oxygen from the oxygen supply canister 246 may be fed back into the catalyst bed 251 through a metering valve 257 to a feedback channel 258, which circulates oxygen to the catalyst bed 251. Also as noted above, the check valve 255 between the exit of the feedback channel 258 and the catalyst bed entrance (oxygen input 254) prevents gases from the catalyst bed 251 from entering and contaminating the oxygen storage canister 246. Concentrated oxygen levels are recycled back and mixed with the inflow from the membrane passing gases, which will support and speed up the catalysis of CO into $CO_2$.

The catalyst may be any catalyst that accelerates the oxidization of carbon monoxide into carbon dioxide, especially at low temperatures. For example, the catalyst may be a precious metal (e.g., palladium, platinum, gold, etc.) deposited on a substrate material (e.g., aluminum oxide, tin oxide, etc.). The CO and $O_2$ attach to the catalyst and the catalyst accelerates the oxidization of the CO into $CO_2$ without being consumed itself. Thus, the catalyst never depletes, and the carbon monoxide is essentially removed from the intake gas mixture (or at least reduced to a level below toxic levels (e.g., <0.04%)).

Further, the self-rescuer device 200 may include a carbon monoxide sensor 259 that measures the level of carbon monoxide at the output 256 of the catalyst bed 251. The self-rescuer device 200 may also include a recirculation valve 261 with a first position and a second position, where the first position allows the flow to flow out of the output, and the second position prevents the flow from flowing out of the output and forces the flow back into the catalyst bed.

In an example embodiment, a controller 290 is coupled to the carbon monoxide sensor 259 and the recirculation valve 261. The controller 290 places the recirculation valve 261 in the first position when the carbon monoxide level of the flow is below a carbon monoxide threshold and places the recirculation valve 261 in the second position when the carbon monoxide level of the flow is not below the carbon monoxide threshold.

For instance, in an example configuration, if carbon monoxide levels are above a predetermined threshold, then a controller 290 activates the recirculation valve 261 to recirculate the flow back to the catalyst bed 251 for further oxidization. However, if the carbon monoxide levels are below the predetermined threshold, then the control electronics deactivate the recirculation valve 261 to allow the flow to the scrubbing bed 252.

While only one catalyst bed 250 is shown in FIG. 2, some embodiments include several catalyst beds 250 in series to help ensure the CO is redundantly removed from the flow. The number of catalyst beds 250 may be dictated by the environment in which the self-rescuer device 200 is to be used: the more carbon monoxide expected, the more catalyst beds 250 may be needed (taking into account any recirculation capabilities).

In certain embodiments, the scrubbing bed 252 comprises an input 263, an output 264, and scrubbing media 265. The input 263 of the scrubbing bed 252 is coupled to the output 256 of the catalyst bed 251 to receive a flow from the catalyst bed 251. Also, the output 264 of the scrubbing bed 252 is coupled to the oxygen holding canister 246.

The scrubbing media 265 absorbs carbon dioxide from the flow. More particularly, the scrubbing bed 252 removes the carbon dioxide (already in the gas flow or introduced because of the oxidization of carbon monoxide into carbon dioxide) from the gas mixture flowing through a scrubbing media (e.g., lithium hydroxide, calcium oxide, etc.). As with the catalyst bed 251, there may be several scrubbing beds in series to remove the $CO_2$ effectively and redundantly. Unlike the catalyst of the catalyst bed 251, the scrubbing media 265 of the scrubbing bed 252 may be depleted over time because of the chemical reaction to remove the $CO_2$. Therefore, it is possible that the self-rescuer device 200 of FIG. 2 may not filter out the $CO_2$ even with power remaining in the power source (not shown for sake of clarity, but similar to the power source 180 of FIG. 1), e.g., where the scrubbing media 265 of the scrubbing bed 252 has been depleted.

For instance, in an illustrative implementation, a first bed contains a catalyst to accelerate the oxidation of CO into $CO_2$. The $CO_2$, now liberated from the catalyst bed, passes into a sequential $CO_2$ scrubbing section where this gas will be absorbed into a scrubbing media (LiOH, CaO, $Li_2O_2$) and bound up as a solid reaction product. Part of the purified $O_2$ exiting out of this gas stream may be fed back into the gas stream entering the catalyzing and scrubbing sections.

In certain example configurations, the self-rescuer device 200 includes a carbon dioxide sensor 266 that measures the level of carbon dioxide at an output 264 of the scrubbing bed 252. The self-rescuer device 200 can also include a recirculation valve 267 having a first position and a second position. The first position allows the flow to flow out of the output, and the second position prevents the flow from flowing out of the output and forces the flow back into the scrubbing bed 252. Moreover, the controller 290 (e.g., a component of corresponding control electronics), is coupled to the carbon dioxide sensor 266 and the recirculation valve 267. In this manner, the controller 290 places the recirculation valve 267 in the first position when the carbon monoxide level of the flow is below a carbon dioxide threshold and places the recirculation valve 267 in the second position when the carbon monoxide level of the flow is not below the carbon dioxide threshold.

For instance, in an example embodiment, if carbon dioxide levels are above a predetermined threshold, then controller 290 activates the a recirculation valve 267 to recirculate the flow back to the scrubbing bed 252 for further scrubbing. However, if the carbon dioxide levels are below the predetermined threshold, then the control electronics deactivate the recirculation valve 267 to allow the flow to the oxygen storage canister 246.

Moreover, the self-rescuer device 200 of FIG. 2 illustrates a variable-rate flow pump 268 that may be used to change the rate at which oxygen is delivered to the breathing mask 250. For instance, in an example configuration, the variable-flow pump 268 is coupled to a sensor 269 and to an input 271 of the primary oxygen storage canister 246. Here, the controller 290 causes the variable-flow pump 268 to change a process-flow rate of the self-rescuer device based on the sensor 269.

It should be noted however that such a variable-flow pump 268 is not required for the self-rescuer device 200 to function.

In the illustrated self-rescuer device 200, the chemical processing arrangement will be sequential, first CO catalysis into $CO_2$, and then $CO_2$ absorption into the scrubbing beds. The concentrated $O_2$ exiting this processing loop will be injected into the nose and mouth covering inside the breathing mask shell and mixed with the $N_2$ stream to maintain a 19.5% to 21% air mixture for supplying habitable air to the user.

As noted above, an alternative arrangement for oxygen concentrating and purifying is to pass the gas stream through a sequential or series arrangement of multiple processing beds where the intake gases from the open environment are continually purified as they are cascaded through inline sections. The number of sequential CO catalyzing beds followed by multiple $CO_2$ scrubbing sections, flow rate, and dwell time is determined both by the efficiency of the circuit and the demands of the system.

Other arrangements combine both in-line, cascading processing sections with recycling circuits to achieve the most efficient oxygen purifying/concentrating treatment of the gas stream passing through the initial first sieve 210. In this implementation, the processing flow is controlled by the processor 290 via a series of electronic valves. The electronic control system, including the processor that governs the operation of the self-rescuer device is discussed in greater detail herein.

Also, the self-rescuer device 200 may include any of the power sources and other features of the self-rescuer device 100 of FIG. 1. However, as mentioned above, the self-rescuer device 200 of FIG. 2 may fail before power is drained because the scrubbing media may be depleted before power runs out. Also, since the CO and $CO_2$ are removed chemically from the gas flow, the CO and $CO_2$ do not need to be vented from the self-rescuer device 200.

Further, any of the components, elements, control features and other details discussed in greater detail herein with regard to the embodiment of FIG. 2 may be added to the embodiment of FIG. 1.

$O_2$, $CO_2$, CO Sieve/CO Catalyzing/RCA Cell $CO_2$ Removal OSSR

Figure 3:
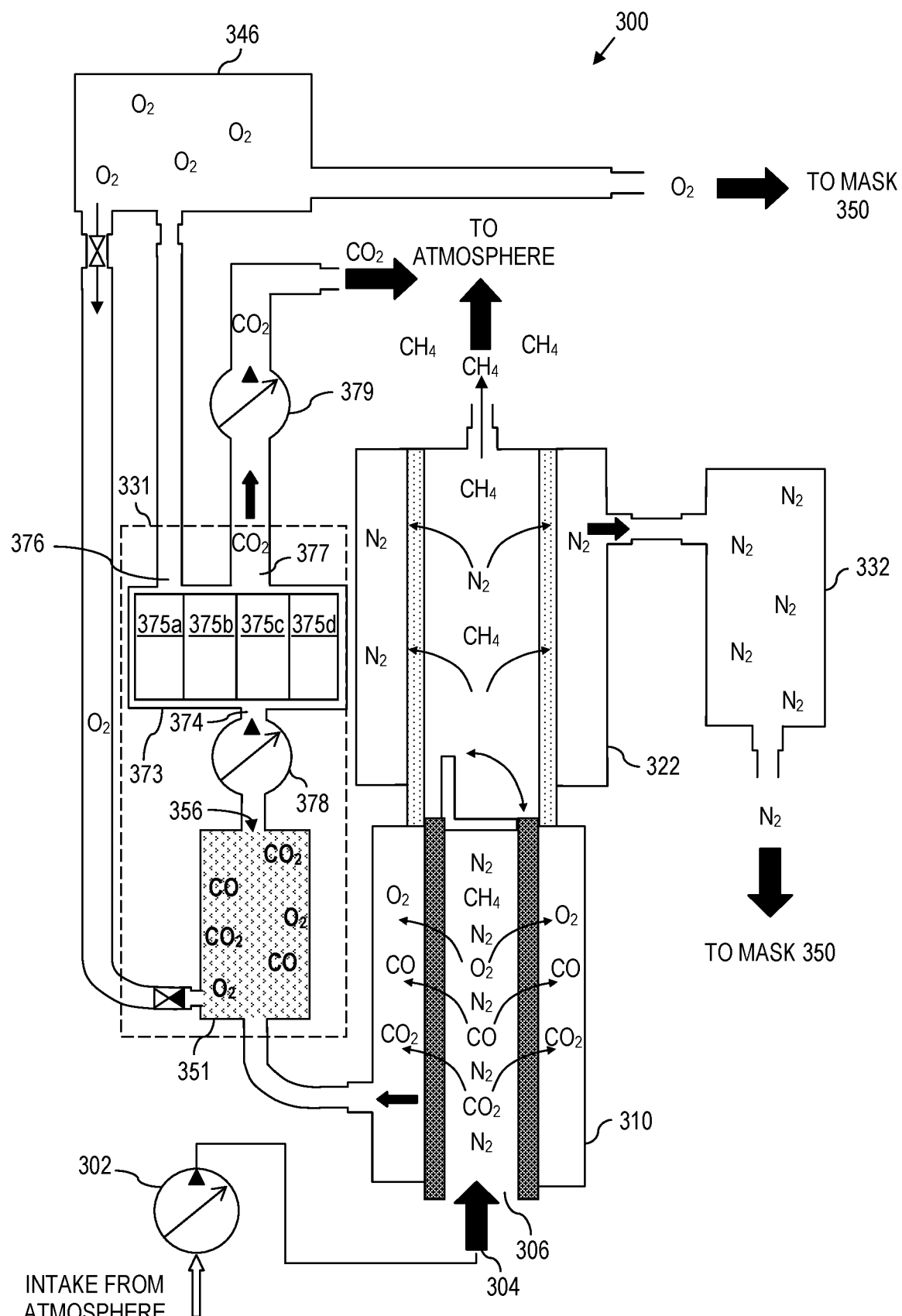
FIG. 3 is a block diagram illustrating a flow of air through a third embodiment of a self-rescuer device including a catalyst bed and a rapid cycle amine bed, according to various aspects of the present disclosure.

In FIG. 3, a self-rescuer device 300 is illustrated according to further aspects of the present disclosure. In this implementation, elements of the self-rescuer device 300 are analogous to like elements of the self-rescuer device 200 of FIG. 2. As such, like elements are indicated with reference numbers 100 higher in FIG. 3 than their counterpart in FIG. 2. For sake of clarity of discussion, certain optional components schematically shown in FIG. 1 are omitted in FIG. 3. However, features and elements from other embodiments can be included in the embodiment of FIG. 3, unless otherwise noted. Likewise, the features and elements of FIG. 3 can be shared with the other embodiments herein unless otherwise noted.

This self-rescuer device 300 features the same $O_2$, CO and $CO_2$ sieve subsystem and a purifying subsystem to supply oxygen. However, the purifying system in this embodiment makes use of a regenerative technology for separating and expelling $CO_2$ from the gas feed stream. One advantage of this variant is that it is not limited by expendable stores of scrubbing chemicals.

The self-rescuer device 300 includes an intake pump 302, a first sieve 310, second sieve 322, nitrogen storage canister 332, oxygen storage canister 346, and catalyst bed 350 as illustrated. The intake pump 302, first sieve 310, second sieve 322, nitrogen storage canister 332, and oxygen storage canister 346 operate similarly to their respective components 210, 222, 232, and 246 of the self-rescuer device 200 of FIG. 2. However, instead of the scrubbing bed (252, FIG. 2), a rapid-cycle amine bed 373 is provided in the gas processor 331.

In general, the rapid-cycle amine bed 373 includes an input 374, a plurality of rapid cycle amine cells 375a-d, an oxygen output 376, and a carbon dioxide output 377. The input 374 of the rapid cycle amine bed 373 is coupled to the output 356 of the catalyst bed 351 to receive flow from the catalyst bed 351.

The amine cells 375 adsorb carbon dioxide from the flow. The oxygen output 376 of the rapid cycle amine bed 373 is coupled to the primary oxygen storage canister 346. On the other hand, the carbon dioxide output 377 vents carbon dioxide rich air from the self-rescuer device 300. For instance, in an example configuration, approximately half of the rapid cycle amine cells 375 are activated in opposite cycles of another approximately half of the rapid cycle amine cells 375 to stabilize heat transfer.

In an example embodiment, the rapid-cycle amine bed 373 comprises several rapid-cycle amine (RCA) cells 375a-d. While four rapid-cycle amine cells 375a-d are shown, the rapid-cycle bed 373 may include more or less RCA cells 375a-d.

In an example configuration, the self-rescuer device 300 comprises a pressure swing pump 378 coupled to the rapid cycle amine cells 375, and a vacuum swing pump 379 coupled to the rapid cycle amine cells 375. The RCA cells 375a-d include solid amine adsorbents with a high affinity for carbon dioxide. During an adsorb cycle, the pressure swing pump 378 provides pressure to the RCA cells 375a-d and the carbon dioxide gets adsorbed by the solid amines. The resulting flow of processed gas is depleted of carbon dioxide and is sent to the oxygen storage canister 346. During a desorb cycle (i.e., regenerating cycle), a vacuum-swing pump 379 provides a negative pressure in the RCA cells 375a-d to vent the carbon dioxide that was adsorbed by the RCA cells 375a-d from the self-rescuer device 300.

In some embodiments, control electronics may place alternating RCA cells 375a-d in the desorb cycle while the other RCA cells 375a-d are in the adsorb cycle. For example, RCA cells 375a and 375c may be in the desorb cycle while RCA cells 375b and 375d are in the adsorb cycle. This alternating cycling of the RCA cells 375a-d allows for a more constant flow of oxygen to the oxygen storage canister 346. Further, the heat generated in the RCA cells 375a and 375c during an adsorb cycle (adsorb cycles are exothermic) may be dissipated in the RCA cells 375b and 375d in the regenerating cycle (regenerating cycles are endothermic). Thus, the overall heat generated in the RCA bed 373 is close to balanced when alternating RCA cells 375a, 375c and 375b, 375d.

Further, the self-rescuer device 300 may include components from any of the embodiments discussed above in reference to FIGS. 1-2. For example, the self-rescuer device 300 may include the carbon monoxide sensor and recycle valve after the catalyst bed 351, a carbon dioxide sensor and recycle valve after the RCA bed 373, power systems as described above, the loop-back channel, the variable-flow pump, combinations thereof, etc.

In certain embodiments, the RCA cells 375a-d are regenerative, meaning that the precious metals and substrate materials do not get consumed during the carbon dioxide removal process. As such, the self-rescuer device 300 will not stop working before the power source is drained. In other words, the self-rescuer device 300 will concentrate oxygen and filter the gas mixture as long as electrical power is supplied to the self-rescuer device 300 (e.g., from an external power source, from an internal power source, or from both). Therefore, the self-rescuer device 300 has many of the advantages of the self-rescuer devices described above.

For instance, solid amine adsorbents have a high affinity for $CO_2$ and can readily be applied as a coating upon a porous, high surface area polymer. The bed of solid amine material is regenerated by applying a vacuum to its container for evacuation. An adsorption cycle fixes the $CO_2$ to surface sites of the RCA bed. Applying a vacuum to the bed causes the attached $CO_2$ and $H_2O$ to desorb from its surfaces and restores the ability of the bed to separate $CO_2$. This regenerative ability thus holds advantages over non-regenerative, fixed capacity $CO_2$ absorption materials like the LiOH and CaO beds used in the previous embodiment.

The Rapid Cycle Amine (RCA) technology also has advantages over older scrubbing technologies with regard to heat management. The adsorption of $CO_2$ into the solid amine bed is exothermic (releasing heat). Alternatively, the desorption phase is endothermic (needing heat). Temperature management can be achieved by thermally coupling alternating beds (adsorbing and regenerating). These physically coupled beds dissipate the heat generated in the adsorption bed by the heat lost in the regenerative bed by conduction. This heat neutral attribute has a significant advantage for heat management in the self-rescuer device 300 compared to measures required to eliminate the heat generated from conventional $CO_2$ chemical scrubbing technologies. Alternatively, ionic liquid cells may be used in conjunction with the RCA beds 375a-d or instead of the RCA beds 375a-d for absorbing/desorbing $CO_2$.

In this example configuration, in an analogous manner to the rapid-cycle amine bed 373, an ionic liquid bed comprises an input, an oxygen output, a carbon dioxide output, and a plurality of ionic liquid cells. Here, the input of the ionic liquid bed is coupled to the output of the catalyst bed to receive flow from the catalyst bed. Also, the oxygen output of the ionic liquid bed is coupled to the primary oxygen storage canister. Further, the ionic liquid cells adsorb carbon dioxide from the flow, and the carbon dioxide output vents carbon dioxide rich air from the self-rescuer device.

Regardless, as noted more fully herein, any of the components, elements, control features and other details discussed in greater detail herein with regard to any of the preceding embodiments may be added to the embodiment of FIG. 3.

$O_2$, $CO_2$, CO Sieve/CO Catalyzing/RCA Cell $CO_2$ Removal OSSR

Figure 4:
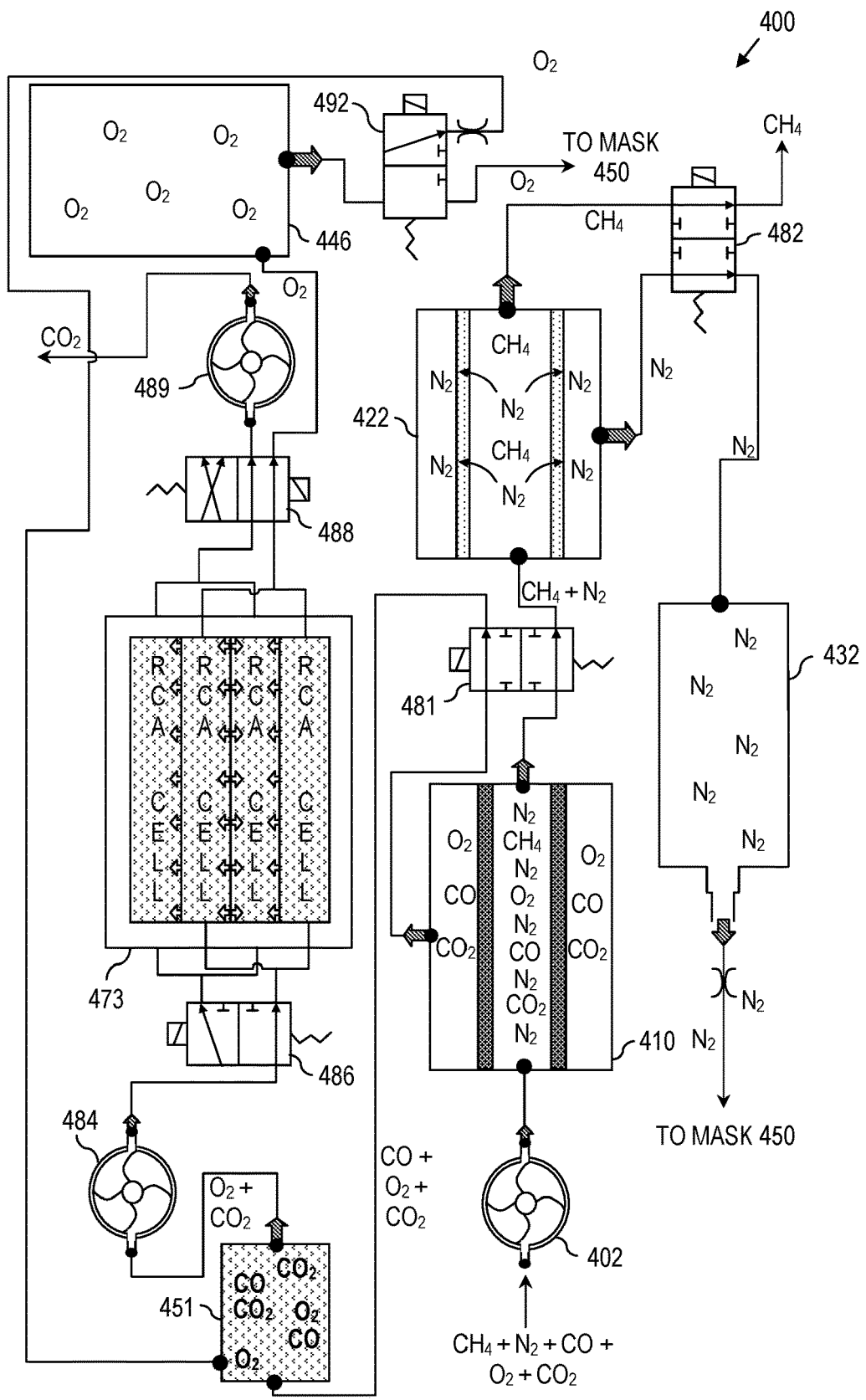
FIG. 4 is a block diagram of an alternative to the embodiment of FIG. 3 illustrating control valves and additional features, according to aspects of the present disclosure.

Referring to FIG. 4, a variation of the self-rescuer device 300 of FIG. 3 is illustrated to show some alternative connections and circuits. In this implementation, elements of the self-rescuer device 400 are analogous to like elements of the self-rescuer device 300 of FIG. 3. As such, like elements are indicated with reference numbers 100 higher in FIG. 4 than their counterpart in FIG. 3. For sake of clarity of discussion, certain optional components schematically shown in FIG. 1 are omitted in FIG. 4. Again, however, features and elements from other embodiments can be included in the embodiment of FIG. 4, unless otherwise noted. Likewise, the features and elements of FIG. 4 can be shared with the other embodiments herein unless otherwise noted.

As illustrated, the intake pump 402 is implemented as a blower having an intake that draws in a gas supply from the toxic environment. The blower includes a pressure side that creates a pressure swing to supply the gas collected at the intake to the sieve system.

A first control valve 481 is electrically controlled to regulate the output of the first sieve 410. For instance, the first control valve 481 controls a pressure swing to the CO, $O_2$, $CO_2$ sieve (first sieve 410). The first control valve 481 also controls the timing of when the $CH_4$ and $N_2$ are supplied from the first sieve 410 to the second sieve 422. Still further, the first control valve 481 controls the timing of when the CO, $O_2$, $CO_2$ from the first sieve 410 is coupled to the catalyst bed 451.

A second control valve 482 controls the pressure swings at the second sieve 422. The second control valve 482 also controls when the sieved $CH_4$ is vented to atmosphere. The second control valve 482 also controls the vents that supply the $N_2$ to the nitrogen canister 432.

A second blower 484 is utilized to move the $O_2$ and $CO_2$ from the catalyst bed 451 to the RCA bed 473. A pressure side of the second blower 484 cyclically loads the RCA bed 473 with $O_2$ and $CO_2$ using pressure swings.

A third control valve 486 is situated between the second blower 484 and the RCA bed 473. The third control valve 486 cycles gas flow to alternating beds of the RCA bed 475. This allows heat to flow from adsorbed beds to desorbed beds via conduction.

The output of the RCA bed 475 flows to a fourth control valve 488. The fourth control valve 488 cycles gas flow to the oxygen canister 446. The fourth control valve 488 further cycle controls the venting of desorbed $CO_2$ and $H_2O$ to atmosphere.

A third blower 489 interacts with the fourth control valve 488 and provides a vacuum-side to cyclically evacuate the $CO_2$ from the RCA beds 473 to atmosphere.

A fifth control valve 492 provides valve services that supply $O_2$ to a breathing mask 450. The fifth control valve 492 also controls the recycling of $O_2$ to the CO catalyst bed 451 (the recycling process is described in greater detail herein).

Further, any of the components, elements, control features and other details discussed in greater detail herein with regard to any of the preceding embodiments may be added to the embodiment of FIG. 4.

$O_2$, CO, $CO_2$ Membrane Sieve/CO Catalyst/Oxygen Electrolytic Sieve OSSR

Figure 5:
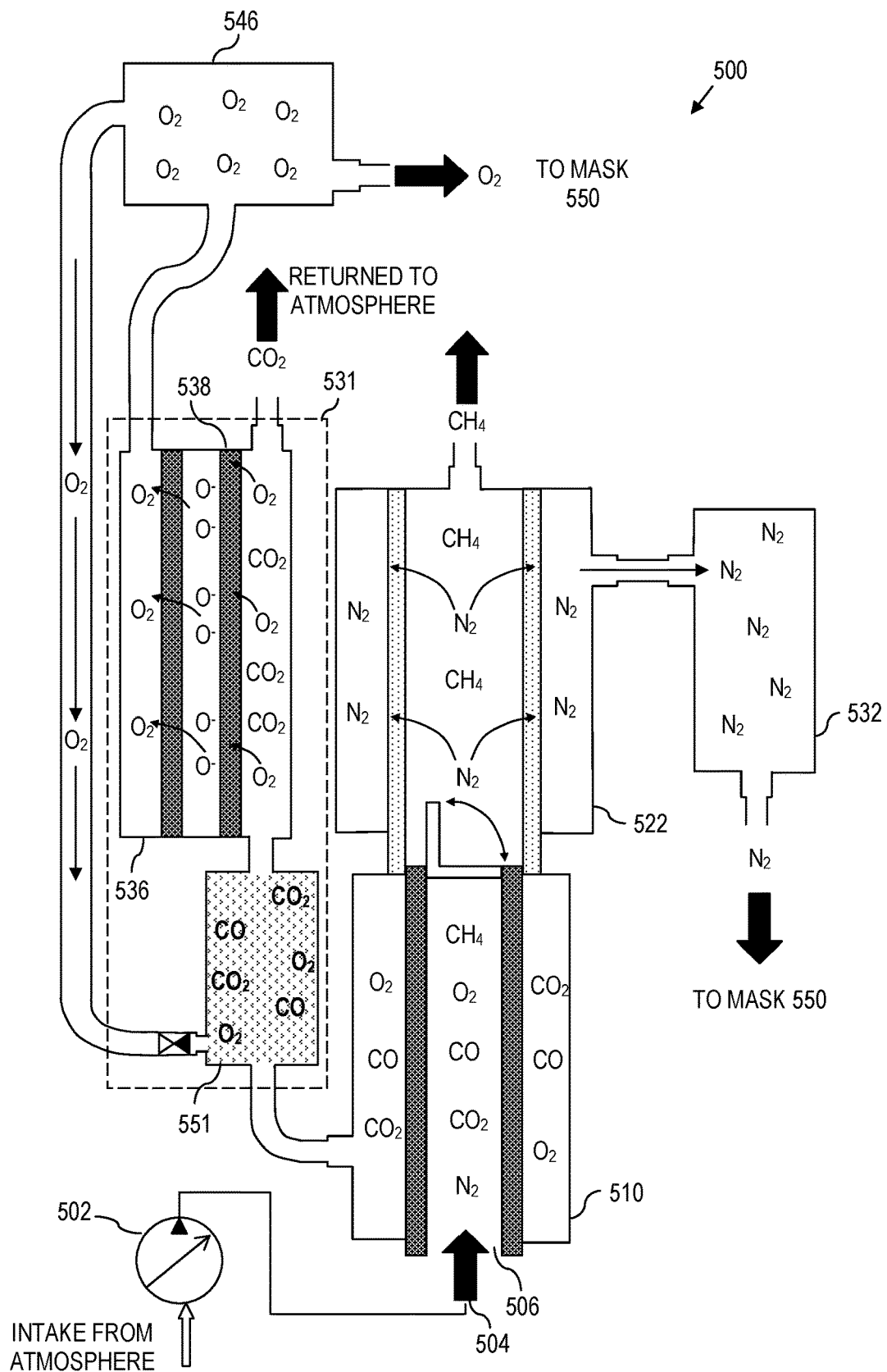
FIG. 5 is a block diagram illustrating a flow of air through another embodiment of a self-rescuer device including a catalyst bed and an electrolytic oxygen sieve, according to various aspects of the present disclosure.

Referring to FIG. 5, a self-rescuer device 500 is illustrated according to further aspects of the present disclosure. In this implementation, elements of the self-rescuer device 500 are analogous to like elements of the self-rescuer device 100 of FIG. 1. As such, like elements are indicated with reference numbers 400 higher in FIG. 5, then their counterpart in FIG. 1. Again, for sake of clarity of discussion, certain optional components schematically shown in FIG. 1 are omitted in FIG. 5. However, features and elements from other embodiments can be included in the embodiment of FIG. 5, unless otherwise noted. Likewise, the features and elements of FIG. 5 can be shared with the other embodiments herein unless otherwise noted.

In certain embodiments, the self-rescuer device 500 is a hybrid of the first two embodiments (FIG. 1 and FIG. 2) that uses both nitrogen sieves and electrolytic oxygen sieves. This system makes use of upstream catalyst bed(s) to prevent contamination of the electrolytic $O_2$ sieve by the feed stream gases such as CO. In some embodiments, this hybrid system uses regenerative catalysts or other regenerative adsorb/desorb separating technologies to prevent contamination of the $O_2$ electrolytic sieve.

Basically, the self-rescuer device 500 functions similarly to the self-rescuer device of FIG. 1. However, the self-rescuer device 500 of FIG. 5 further includes at least one catalyst bed 551 (similar to the catalyst beds 251, 351 of FIGS. 2-3) and/or scrubbing bed (e.g., analogous to scrubbing bed 252 FIG. 2) upstream between the entrance to the electrolytic sieve 536 and downstream to the first sieve 510. The at least one catalyst bed and/or scrubbing bed can be provided upstream of the electrolytic sieve, for example, to remove contaminating gases that can poison or greatly reduce the viable operating time of the electrolytic sieve.

The catalyst bed 551 oxidizes CO into $CO_2$ in the same fashion as described above in reference to FIG. 2. This embodiment provides an advantage over the embodiment of FIG. 1 in that some electrolytic sieve membrane materials may become contaminated if too much carbon monoxide is present. In this regard, a reduction in carbon monoxide within the electrolytic sieve 536 is provided by the catalyst bed 551, thus helping to prevent this contamination. The self-rescuer device 500 does not have chemical storage limits (similar to the embodiments of FIGS. 1, 3, and 4), so the self-rescuer device 500 can concentrate oxygen and filter the gas mixture flow as long as power is supplied to the self-rescuer device 500.

In other example embodiments, a scrubbing bed is located before the electrolytic sieve 536 if the membrane 538 of the electrolytic sieve 536 is made of a material that may be contaminated by carbon dioxide. Further, any of the components, elements, control features and other details discussed in greater detail herein with regard to any of the preceding embodiments may be added to the embodiment of FIG. 5.

Some electrolyte sieve materials are susceptible to contamination by gases commonly found in post explosion/fire environments. These materials are easily poisoned by gases in their supplied feed stream such as CO. Depending upon their particular susceptibility, platinum or other catalyzing metals may coat the intake sections of the sieve to catalyze contaminating gases like CO into more benign gases like $CO_2$. Alternatively in line catalyst beds can be positioned in the gas feed stream, upstream of the electrolytic sieve. These upstream beds serve to prevent or reduce sieve/electrolyte contamination. This embodiment's arrangement of the oxygen concentrating and purifying subsystem is a hybrid of the nitrogen membrane sieve/oxygen electrolytic sieve OSSR and the nitrogen membrane sieve/CO catalyzing/CO2 scrubbing OSSR.

Depending upon the susceptibility of the electrolytic sieve material to a particular contaminant, catalyst coatings and/or catalyst beds can be arranged in the intake section of the cell to speed up the oxidation of certain gases into less contaminating products for the electrolytic cell. This arrangement possesses the advantages of the nitrogen membrane/oxygen electrolytic sieve in that it has no chemical storage limits, as the catalyst material is not chemically changed, but speeds up the oxidation reaction of the contaminates. It is technically only limited in duration by the capacity of its batteries or other power source.

Some electrolytic cell materials may be susceptible to other gases present in the feed stream such as $CO_2$. Beds of scrubbing chemicals used to remove some of the $CO_2$ from the cells feed stream may improve the operational duration of the cell. Like the nitrogen membrane/CO catalyzing/$CO_2$ scrubbing OSSR, this arrangement is also limited by the amount of scrubbing chemicals. When these scrubbing stores reach their capacity and are expended, the poisoning gases will again flow to the electrolytic sieve, ultimately ceasing its operation. However, this arrangement may ultimately remain in operation far longer than the OSSR featuring no electrolytic sieve in the $O_2$ concentrating/CO catalyzing/$CO_2$ scrubbing implementation. The tolerance levels for the cell material may be higher than that allowable for the habitable feed stream, increasing the effective operating time over the second embodiment.

Example Breathing Mask

FIG. 6 illustrates self-rescuer device 600 including a breathing mask 602 and an exterior mask shell 604. Analogous to the other embodiments herein, features and elements from other embodiments can be included in the embodiment of FIG. 6, unless otherwise noted. Likewise, the features and elements of FIG. 6 can be shared with the other embodiments herein unless otherwise noted.

Thus, the breathing mask 602 is positioned inside the mask shell 604. The mask shell 604 includes a transparent polycarbonate structure 606 that fits over a user's face. The mask shell 604 also includes vent valves 608 that aid in the pressurization of the self-rescuer device 600. Excess nitrogen may be used to provide positive pressure to the breathing mask 602 and impede infiltration of toxic gases into the breathing mask 602. Nitrogen flows from a nitrogen storage canister (132, 232, 332, 432, 532 in FIGS. 1-5 respectively) through nitrogen supply lines 610, 612 and out nitrogen outlet ports 614, 616 to pressurize the self-rescuer device 600. The vent valves 608 allow excess nitrogen to escape from the self-rescuer device 600 and be vented to the exterior atmosphere when the self-rescuer device 600 reaches a predetermined pressure. This pressurization makes the self-rescuer device (100, 200, 300, 400, 500 in FIGS. 1-5 respectively) more effective for users with beards, unusual facial features, or both. Further, the pressurization prevents toxic gas from the atmosphere from entering the breathing mask 602, prevents the exterior shell 604 from fogging up during use, and offers protection of the user's eyes from smoke, dust, dirt, etc. In this regard, one or more vent valves 608 may be provided. Moreover, the location of the vent valves is optimized for optimal shell pressurization.

The breathing mask 602 receives nitrogen from the nitrogen supply lines 610, 612 and oxygen from an oxygen supply line 618 at a ratio of about 21:79. In an illustrative implementation, the nitrogen supply lines 610, 612 are implemented as a single supply line. Here, the oxygen supply line 618 is provided inside the nitrogen supply line. The self-rescuer device 600 also includes nitrogen outlet ports 620, 622 that allow the oxygen and nitrogen mixture to flow into the mask interior to supply habitable air to a user. An oxygen injection valve can be used to ensure that the mixture of oxygen and nitrogen meets the desired balance.

Further, the self-rescuer device 600 may include pressure sensors 624, flow sensors 626, oxygen sensors 628, or combinations thereof that measure the ratio of oxygen-to-nitrogen, inhalation/exhalation rate, and adjust the flow of oxygen and nitrogen accordingly to maintain the proper ratio. Moreover, as discussed above, the sensors may determine that the user is undergoing high levels of exertion and adjust the flow rate (e.g., using a variable-flow pump) of the oxygen and nitrogen to the user. Further, in times of low exertion, the self-rescuer device may scale back on the oxygen and nitrogen supplied to save power for later. In other words, the flow is arranged to supply oxygen at a 21% concentration relative to the total inhaled volume. A check valve 630 helps ensure that any exhalations from the user do no return up the oxygen supply line 618. In this embodiment, oxygen is continually supplied to the breathing mask 602.

In a second embodiment of the self-rescuer device 600, the sensors 624, 626, 628 may be used for sensing a breathing cycle of the user and optimizing oxygen use. For example, oxygen may be supplied to the self-rescuer device 600 based on the user's breathing cycle detected by the sensors 624, 626, 628. The second embodiment of the self-rescuer device 600 optimizes the use of oxygen and prolongs the working duration of the system.

As shown, the self-rescuer device 600 includes the exhalation vent 632 that vents the user's exhalations. However, as discussed herein, the user's exhalations may be looped back into the self-rescuer device to recover the oxygen that the user will exhale. The self-rescuer device 600 may be used with any of the embodiments of the self-rescuer device discussed herein. For instance, to optimize oxygen use efficiency, it may be practical to recycle the exhaled oxygen in certain embodiments, with the system processing makeup oxygen from the external environment.

In this regard, the self-rescuer device includes at least one feedback passage (e.g., via the loop-back 160) for recycling the oxygen and nitrogen from the exhaled air of the user, with makeup oxygen and mask purging nitrogen coming from the external atmosphere in "open loop" operation.

Detoxification Process

Figure 7:
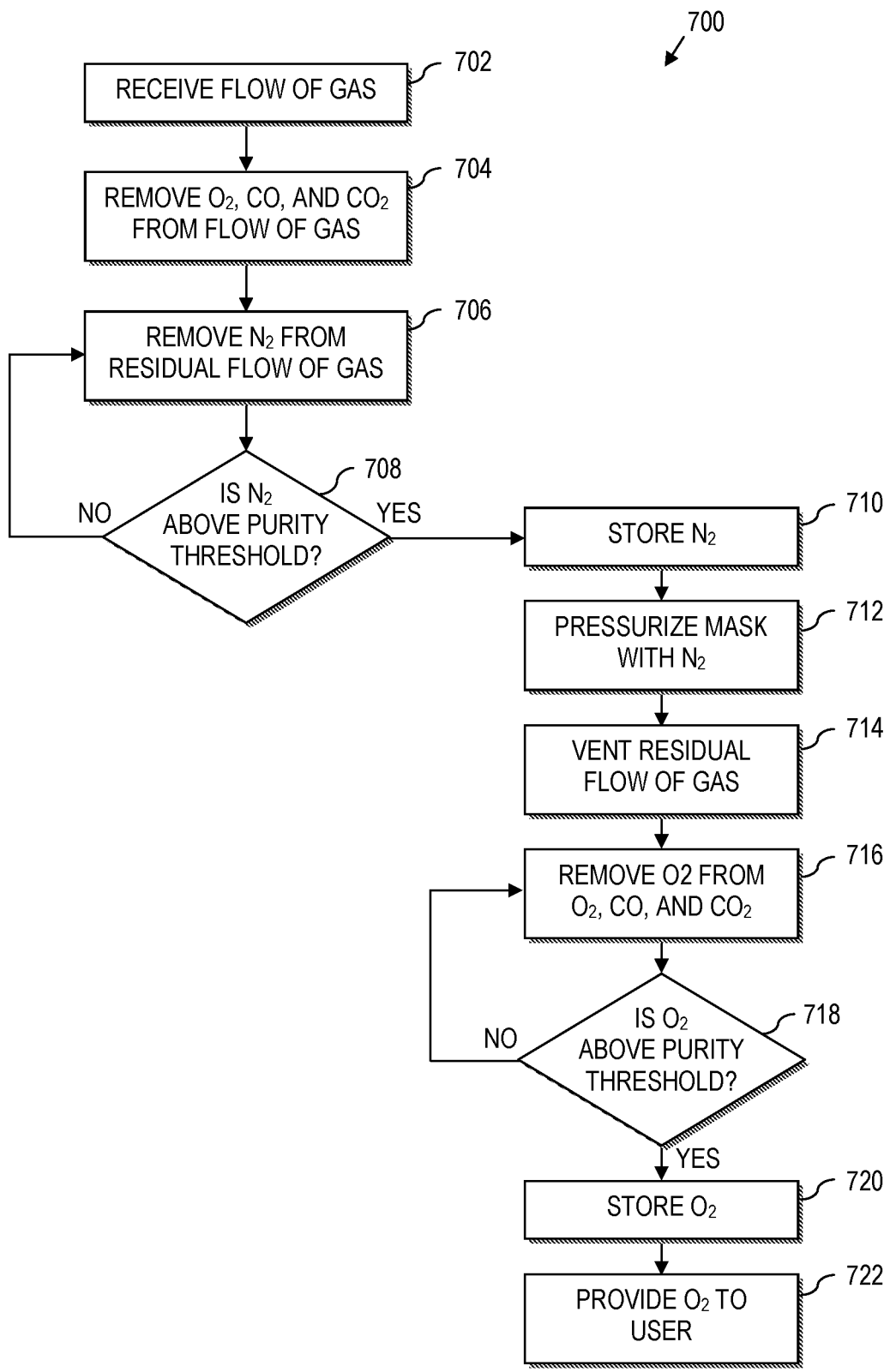
FIG. 7 is a flow chart illustrating a method of providing oxygen and nitrogen to a user of a self-rescuer device, according to various aspects of the present disclosure.

FIG. 7 is a flow chart illustrating a process 700 for processing a gas mixture and concentrating oxygen for a self-rescuer device. The self-rescuer device receives a flow of gas at 702. At 704, the self-rescuer device removes the oxygen, carbon monoxide, and carbon dioxide from the flow of the gas to create a mixture of oxygen, carbon monoxide, and carbon dioxide. At 706, the self-rescuer device removes nitrogen from a residual flow of the gas (i.e., by removing nitrogen from the oxygen, carbon monoxide, and carbon dioxide depleted gas stream). At 708, the self-rescuer device determines if the removed nitrogen has a purity level above a predetermined threshold. If so, then the self-rescuer device stores the nitrogen for later use at 710, e.g., in the nitrogen storage canister. For instance, the method 700 may comprise storing the nitrogen in a nitrogen storage canister separate from the oxygen storage canister. However, if the removed nitrogen has a purity level below the predetermined threshold, then the self-rescuer device returns to 706 to purify the nitrogen further. Once the nitrogen is stored at 710, the nitrogen may be used to pressurize a breathing mask of the self-rescuer device at 712 (e.g., by pressurizing the breathing mask with the nitrogen from the nitrogen storage canister), to mix with oxygen for a user to breathe, or both. At 714, the residual flow of gas (i.e., the flow of gas with the nitrogen, oxygen, carbon monoxide, and carbon dioxide removed) is vented from the self-rescuer device.

The self-rescuer device removes the oxygen from the mixture of oxygen, carbon monoxide, and carbon dioxide removed from the gas flow stream at 716. Any method, including those described herein, may be used to remove the oxygen. For example, catalyst beds, RCA beds, ionic liquid cells, scrubbing beds, electrolytic sieves, other sieves, or combinations thereof may be used to remove the oxygen from the mixture. At 718, if the oxygen has a purity level below a predetermined threshold, then the self-rescuer device recirculates the mixture to 716 until the oxygen has a purity level above the predetermined threshold. Once the oxygen has a purity level above the predetermined threshold, the oxygen is concentrated and is stored at 720 (e.g., by concentrating the oxygen in a storage tank). Moreover, the oxygen is provided to the user at 722. In certain example embodiments, the method 700 comprises supplying the nitrogen and oxygen to a user through a breathing mask, wherein a ratio of nitrogen-to-oxygen is approximately 79:21.

While the flow chart illustrates the process 700 as being a serial process, the elements performed in the flow chart may be performed in sequences different than shown, including performing some in parallel. For example, boxes 706-714 can be performed in parallel with boxes 716-722.

Electronic Control System

Regardless of which self-rescuer device embodiment herein, an electronic control system is provided that autonomously operates the included nitrogen/oxygen separating and purifying subsystems. The electronic control system also monitors the final gas makeup that is supplied to the user as well as the current user uptake.

An example implementation of the control system comprises a processor that monitors the purity of the gas stream exiting the catalyzing/absorbing beds. The processor, e.g., implemented as a microcontroller, closes the intake valve and closes the $O_2$ storage canister once it has been pressurized to a target value. The processor then opens a bypass valve to recycle the flow exiting the catalysis/scrubbing beds back into the intake stream, improving its efficiency and preserving the precious oxygen. The electronic control system keeps recycling this flow until the CO and $CO_2$ levels are at or below acceptable levels.

In another example configuration, the electronic control system monitors the purity of the oxygen produced by the system and recycles the output flow back through the gas processor until it reaches acceptable breathing purity. In addition or alternatively, the electronic control system can monitor the nitrogen purity separated from the intake gas stream and recycle the gas back through the membrane sieve to increase its purity to acceptable levels for breathing.

Another example implementation of the electronic control system monitors the purity of the $N_2$ concentrating process. The $N_2$ recycles process $N_2$ back through the sieve membrane via a sequence of valves. This provision enables control of the nitrogen purity and the reduction of any trace of the toxic gas levels to acceptable habitable levels. With recycling or cascading processing, the controller adjusts the gas processing rate to a level that would meet the breathing requirements for the survivor donning the system.

In certain embodiments, the on-demand feature of the breathing system then opens the outlet valve to provide $O_2$ for inhalation when the mask sensors inform the controller that an inhalation cycle is occurring. The control system also modifies the process cycle rate to that of the demand of the user. This approach may offer the most efficient arrangement as the supply is increased to match the breathing rate for users experiencing heavy physical exertion, and reduced as the supply rate declines for stationary users under a low physical load.

Also, in certain embodiments, the electronic control system can control the operation of one or several blower(s), compressor(s), or a combination thereof, used in the system. Intermittent and/or variable rate control can optionally be utilized to maximize operation time (and/or battery life). Such intermittent and/or variable rate control can also be used to allow the system to adjust to the momentary breathing demands of the user.

Yet further, in some embodiments, the electronic control system is used to monitor sensors in the breathing mask that operates control valves that injects oxygen into the inhaled gas stream and adjusts the timing of the processing cycles to the changing demands of the user.

Miscellaneous

A self-rescuer device as described herein can operate in an open-loop mode so as to concentrate nitrogen and oxygen directly from the post explosion/fire atmosphere and supply the proper proportions of $N_2$ and $O_2$ to the user for respiration. Here, the integration of sieving/electrolyzing/filtering technologies significantly extends the operational life of emergency breathing apparatuses over the current state of the art. Increasing the operational duration of an emergency breathing system offers a significantly increased opportunity of escape and survival for workers isolated by an explosion or fire. The self-rescuer device can operate in a closed-loop mode supplying habitable air until the processing technology is ready to deliver habitable air to the user.

In membrane separation of the sieves herein, a difference in partial pressures is induced between the two sides of a separating membrane. This forces the sieved gases (i.e., smaller gas molecules) through the membrane, while the larger gas molecules continue in the through stream. Other sieve arrangements feature adsorb/desorb cycles for their cells. In this arrangement, the gases do not pass directly through the sieve. These cells function by first applying a pressure to the cells to force certain gas molecules into the precisely sized pores of the cells, while larger sized gas molecules flow through the feed stream (interior region of a tube). In an alternate cycle, the adsorbed gas(es) are purged from the sieve materials by removing the pressure, or applying a vacuum.

Additionally, certain materials attract certain gases under pressure to their surfaces. When a large surface area substrate is coated with this certain material type, the area available for adsorption is large. Like the pressure cycling sieve technology, this surface attraction technology can also be used to fix certain gases during a pressure phase, and purge them from the cell during a pressure release or vacuum phase. In certain embodiments, the previously described systems incorporating membrane separation technology are replaced by one or more of the alternative technologies to increase efficiency.

Other sieve separation technologies can also be utilized, including for instance, Pressure Swing Adsorption (PSA), Vacuum Swing Adsorption (VSA), and hybrid Vacuum Pressure Swing Adsorption (VPSA). Each has its advantages/disadvantages with regard to gas separation efficiency and resulting gas purity.

Pressure Swing Adsorption takes advantage of a principle wherein under pressure, gases tend to be attracted to specific solid materials. Porous materials, such as activated carbon, alumina and zeolites, have very large surface areas because of their internal porosity. They can be configured to preferably attract specific gases. Upon pressurization this gas is adsorbed into the material until it is saturated. The "trapped" gas is desorbed from the bed material by lowering the external pressure. Releasing the pressure also regenerates the material and prepares it for the next cycle.

Additionally, molecular sieve materials can be incorporated that limit the absorption of certain larger sized molecules because of their small internal pore size. Likewise, specific size gas molecules can be forced into a porous substrate featuring precisely sized pores during a pressure phase. This adaptation can further refine gas detoxification produced by the PSA process.

Pressure Swing Adsorption systems typically feature two adsorbent or absorbent containing vessels to produce a continuous product gas stream. One vessel is being pressurized for the adsorption/absorption phase while the other is being vented for the desorption phase. Pressure Swing Adsorption systems require a compressor to pressurize the intake gas mixture for the adsorption/absorption phase. A Pressure Swing Adsorption equipped system typically requires more power compared to other technologies because of its need to have a compressor.

Vacuum Swing Adsorption systems work by using a vacuum to draw gases through the separation process. Vacuum Swing Adsorption systems function on the steepest part of isotherm curves and thus maximize efficiency. As Vacuum Swing Adsorption operates at near ambient temperatures and pressures, water condensation is not usually an issue with these systems. Because of their high efficiency, these units typically employ a blower to induce the vacuum. Their higher efficiency also means that they can often operate with a single vessel, further reducing the footprint, weight, and complexity of this system.

Hybrid Vacuum Pressure Swing Adsorption systems are among the most efficient associated with gas separation. These systems apply pressurized gas to the separation process, and apply a vacuum to the purge gas cycle. This technology typically uses a rotary lobe blower to both pressurize and evacuate the adsorbent or absorbent bed container. Like Pressure Swing Adsorption systems, Vacuum Pressure Swing Adsorption units may use two adsorbent/absorbent bed vessels to cycle between the pressurizing/vacuum cycles. Some Vacuum Pressure Swing Adsorption systems have the ability to concentrate oxygen from intake gas mixture and discharge waste gases back to the atmosphere comprising nitrogen, water, and carbon dioxide.

Because multiple cycles may be required to concentrate oxygen to a sufficient level at its starting concentration of 8% to 14% in an anticipated post explosion/fire atmosphere, nitrogen will exist in excess relative to the proportions needed for habitable air in the disclosed open loop sieving arrangement. Instead of venting this excess $N_2$ directly to the atmosphere, the excess will be fed to the breathing mask to maintain a positive pressure and prevent the inflow of toxic external gases. Sensors arranged in the breathing mask can indicate the beginning of the inhalation part of the breathing cycle. When this condition is sensed, a valve in the oxygen circuit opens and supplies pure oxygen into the feed stream to the user that contains the breathing mask flushing nitrogen. The flow volume and injection point geometry is arranged to supply oxygen at a 21% concentration relative to the total inhaled air volume, maximizing $O_2$ supply efficiency. Varying the input gas throughput cycling rate to the momentary breathing requirements of the user addresses the demand during periods of heavy physical exertion, or alternatively at periods of rest and inactivity.

An advantage of a positive pressure system over current self-rescuer device technology is the elimination of the need to forcibly "breathe" the system to initiate $O_2$ generation. The high resistance to inhaling air from the present technology is the primary reason that survivors donning the system in past disasters felt that the SCSRs were not working. However, later examination of the discarded units found them to be fully operational, only very difficult from which to draw in life-sustaining air. The positive pressure inside the breathing mask for this invention eliminates any resistance to inhalation. This capability also assists the breathing of survivors who may have compromised respiratory capacities because of smoking, black lung, emphysema, and other respiratory ailments.

Certain embodiments of the present disclosure provide "assisted" breathing where the controller's sensors measure a momentary pressure drop in the mask and pressurized air is supplied to aid the user in the inhalation part of the respiration cycle. Also, sensors in the controller and mask will sense the slight pressure increase due to the exhalation portion of the breathing cycle and drop the supplied pressure to help the user in expelling gases from his lungs. This arrangement can assist users with compromised lung function (e.g., chronic obstructive pulmonary disease (COPD), black lung in miners, etc.) and users under heavy work load (such as first responders). Additionally, the device in certain embodiments supplies oxygen to the interior mask at the proper+/−21% during the inhalation mode only. Oxygen will not be supplied during the exhalation mode as to conserve this depleted gas that is concentrated from the post explosion environment.

In some embodiments, the OSSR increases the percentage of oxygen supplied if the controller senses the need for additional oxygen (compromised respiratory system, heavy physical load) by the user. This could be sensed by the breathing rate and/or by an additional sensor that is measuring the blood oxygen content (i.e. clip on the ear lobe). This ability is meant to assist egress of miners from a post explosion event and maintain efficient work capability for first responders during an emergency.

Example Use

Although counter-intuitive, the occurrence of an explosion, detonation, or fire does not consume all of the oxygen from the atmosphere. Stoichiometric mixtures (perfect proportions of fuel and oxidizer) produce fully reacted products that are essentially inert to namely $H_2O$ and $CO_2$. However, stoichiometric concentrations are rare in real world examples like those experienced in coal mines where typically flammable methane and air form the explosive gas mixtures. Methane explosive concentrations range from 5% to 15% in air, with air serving (oxygen is 21% in the air) as the oxidizer. In the underground mining environment, high-rate ventilation requirements limit areas where explosive concentration of methane can accumulate. Build up to explosive concentrations can occur if a ventilation system of the underground mining environment malfunctions, and in areas that are isolated from the high volume, ventilating air flow, or in rare instances where a sudden inrush of methane may locally overwhelm the ventilating air flow.

An example of a potential explosive scenario includes abandoned sections of the underground mine that are isolated from active working mine areas by masonry seals. Sweeping ventilation air for the active working mine areas does not flow into these isolated areas because of the presence of the seals. After sealing, the isolated area will ultimately transition through the explosive range of methane because of methane leaks from exposed coal faces in the interior airtight region into the trapped, stagnant air. Eventually, the methane percentage will exceed the upper explosive limit (15%) and not be susceptible ignition to an unanticipated or inadvertent spark source. All energy transmitting sources, such as power and communications cables are removed from these areas before the seals are put in place to eliminate man made ignition sources. However, because these abandoned areas can be very large, the total elimination of an inadvertent ignition sources is not possible because natural sources like arcs that can be generated from large rock falls. Therefore, when the abandoned area is within the explosive methane range (5% to 15%), large explosions can occur that produce a very large volume of toxic, post explosion gas. These large volumes of toxic gases are injected into the active sections of the mine when the explosion breaches the seals, endangering the lives of the miners working there. This was the type of methane explosion experienced in the Sago Mine Disaster in 2006. Toxic post-explosion gases infiltrating from the abandoned into active areas of the mine, were responsible for taking the lives of twelve miners who survived the initial explosion only to succumb later to the lethal atmosphere.

Methane explosions can also occur in relatively small, partially confined areas unswept by the diluting ventilation flow, such as raised areas in the mine roof where the normal ventilation air passes underneath. Methane infiltration into these limited areas can readily result in explosive concentrations and be initiated by sources such as the arcs from the interfaces of trolley wires and the connection pole to supply/transportation vehicles that run in track entries. These limited reduced circulation "pockets" almost always ensure that any explosion is limited, and that the toxic gases generated by an explosion are quickly diluted by the ventilating inflow and the massive unaffected volume of the underground workings. The greater danger results from a localized violent explosion from the ignition of fugitive airborne coal dust that can affect a greatly expanded area and reach into mine regions that are not properly rock dusted. Rock dusting is the practice of covering the exposed coal faces with pulverized limestone dust that serves as a diluent agent to prevent the buildup of explosive concentrations of coal dust. The toxic gases generated from a transitioning methane to coal dust explosion can originate in a limited area associated with the methane buildup and expand out to affect extended areas of the mine with flammable levels of coal dust. The expanded toxic gas region resulting from a propagating coal dust explosion was responsible for taking the lives of some of the miners in the recent Big Branch mine disaster in Raleigh County, W. Va. Coal dust explosive propagation and its wide ranging effects (blast trauma and toxic gas generation) were responsible for the high fatality rate for miners in coal mine explosions ranging from the turn of the last century up to the 1969 Health and Safety Act.

A typical gaseous explosive mixture commonly experienced in underground coal mines and natural gas explosions in other confined spaces is methane and air. The methane mixes with the oxygen in the air to form gaseous reaction products, which under ideal (completely mixed) conditions is described as: $CH_4 + 2O_2 \rightarrow CO_2 + 2H_2O$. This "perfect" (balanced) reaction results in product gases that contain no carbon monoxide or oxygen. Only non-ideal (incompletely mixed) fuel rich mixtures produce carbon monoxide and hydrogen in the resulting product gases because of insufficient oxygen (fuel rich) to oxidize all the fuel carbon to carbon dioxide and all the fuel hydrogen to water. It is emphasized that this mechanism for carbon monoxide generation is responsible for taking so many lives of underground mine workers that may initially survive explosions. As described, methane explosions can disperse coal dust which then becomes the primary fuel medium for a secondary explosion as it is suspended by the propagating methane/air explosion front. Fuel rich explosion product gases from coal dust explosions also include ultra-high carbon monoxide, hydrogen, and methane levels as well as traces of other hydrocarbon gases.

Fuel rich (non-ideal) methane/air and coal dust/air combustions are sources of poisonous CO resulting in atmospheres, and are more lethal than the $CO_2$ laden ones that occur under ideal conditions. Reduced levels of oxygen are always the case in the post explosion/combustion/fire atmospheres. Fires extinguish in atmospheres containing less than 14% oxygen. Because there is a finite amount of methane and/or coal dust, not all the 21% oxygen in the starting mine atmosphere is consumed, causing post explosion gas mixtures of typically 8% to 14% oxygen. The innovative methods described herein make use of this remaining oxygen present in the post explosion/fire atmosphere to extend the operational life of emergency rescue breathing technologies.

The self-rescuer device described more fully herein (regardless of embodiment) can be used to provide life sustaining breathing air for workers who survive such catastrophic events, rescuer devices who must pass through the same toxic atmosphere to rescue the survivors, other rescuer devices who work to put out fires and/or search for survivors in building fires, workers who must enter toxic and/or oxygen depleted atmospheres and for other emergencies. Such life threatening breathing environments are often found in post explosion or post fire atmospheres inside confined spaces. Thus, for instance, a self-rescuer device, as described herein, can be used to provide a breathing apparatus for first responders fighting fires, survivors of explosions and/or fires in underground mines, or others trapped by fires inside confined spaces. The self-rescuer device herein significantly extends the operating life of emergency breathing technologies by sieving oxygen from the post explosion/fire environment and filtering and/or expelling toxic gases from its intake gas stream. In illustrative implementations, molecular sieve technology is combined with other catalyzing, gas separating and scrubbing technologies to facilitate the transformation of a lethal environmental atmosphere into a life-sustaining one. The ability to more than double the operational life over current technologies affords higher opportunities for escape and survival scenarios for workers that initially escape a catastrophic explosion or fire. It can also extend the time on site for first responders that currently must egress to replenish/replaced expended air tanks.

The self-rescuer device herein provides numerous advantages over Filter Self-Rescuer devices (FSR), which do not provide life sustaining oxygen. For instance, in practice, a person must receive oxygen in a sufficient concentration (19.5% to 21%) to allow unimpaired physical coordination and mental judgment to allow the possibility of an effective escape. While an initially trapped worker may have a chance to survive at lower oxygen concentrations, the impaired physical and mental capacities associated with these reduced levels may fatally affect a survivor's ability to escape before a FSR device becomes contaminated, making it inoperable. Moreover, one known catalyst for FSRs hopcalite is a mixture of copper and manganese oxides whose catalytic reaction is exothermic. Thus, hopcalite containing FSRs typically feature heat exchangers to make the operating temperature tolerable by the user (i.e., reduce the amount of heat from the exothermic reaction to the user). As the concentration of CO in the immediate atmosphere increases, the operating temperature of the FSR increases. In a short amount of time, the working temperature becomes so uncomfortable that it can produce blisters inside the user's mouth. Regardless of catalyst, such systems do not provide a means to replenish the necessary levels of oxygen to sustain life.

An alternative technology, known as a Self-Contained Self Rescuer devices (SCSR) requires a compressed oxygen bottle or solid oxygen generating chemicals for on board $O_2$ supply. They are closed loop and typically employ a system to scrub $CO_2$ from the user's exhalations. Moreover, such SCSR systems require a set of nose clips to prevent the user from inadvertently inhaling toxic gases from the surrounding post explosion/combustion atmosphere. Such a device is difficult to don in stressful environments. Moreover, a lack of a positive pressure mode requires the user to forcefully "breathe" the system for proper operation, thus making such prior systems difficult to use. Still further, such devices do not handle the presence of CO when the oxygen generating capacity is expended even when survivable levels of oxygen are present. Hybrid Self-Rescuer devices (HSR) combine the attributes of an FSR with an SCSR to allow continued operation if oxygen stores are expended, atmospheric oxygen is in the survivable range, and lethal levels of CO are present. These HSRs may extend the operational life over a SCSR or a FSR alone, but the ideal condition described above must be present for the HSR to work properly.

The control electronics and sensors discussed herein may include processors, sensors, microcontrollers, field-programmable gate arrays, digital signal processors, etc. If code is required for the control electronics to function, the code may be stored on a computer-readable storage medium internal or external to the control electronics.

Aspects of the present invention are described herein with reference to flowchart illustrations of methods and computer program products according to embodiments of the invention. Each block of the flowchart illustrations can be implemented by computer program instructions. These computer program instructions may be provided to a processor to produce a machine, such that the instructions, which execute via the processor of the computer or other programmable data processing apparatus, create means for implementing the functions/acts specified in the flowchart.

These computer program instructions may also be stored in a computer readable storage medium (i.e., computer readable storage device) such that the instructions stored in the computer readable medium produce an article of manufacture including instructions, which implement the function/act specified in the flowcharts when implemented by a processor. Computer-readable storage media specifically do not include signal media. In the context of this document, a computer readable storage medium may be any tangible medium that can contain, or store a program for use by or in connection with an instruction execution system, apparatus, or device.

However, a computer readable signal medium may include a propagated data signal with computer readable program code embodied therein, for example, in baseband or as part of a carrier wave. However, a computer-readable signal medium is not a computer-readable storage medium, and vice-versa.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A process for converting post-explosion gases of an inhabitable level, low-oxygen ambient environment to a breathable mixture for human consumption, the method comprising:
   receiving a flow of post-explosion gas with oxygen, carbon dioxide, carbon monoxide, nitrogen, and methane;
   removing oxygen, carbon monoxide, and carbon dioxide from the flow of post-explosion gas to create:
      a mixture including oxygen, carbon monoxide, and carbon dioxide; and
      a residual stream including nitrogen and methane;
   removing the oxygen from the mixture of oxygen, carbon monoxide, and carbon dioxide;
   concentrating the oxygen in a primary oxygen storage canister;
   removing the nitrogen from the residual stream;
   storing the nitrogen in a nitrogen storage canister separate from the primary oxygen storage canister;
   venting the methane back to the inhabitable level, low-oxygen ambient environment; and metering the stored nitrogen and the stored oxygen to a user through a breathing mask at a habitable level of 19-21% oxygen.

2. The process of claim 1 further comprising:
supplying oxygen from the primary oxygen storage canister to a catalyst bed;
preventing contents from the catalyst bed from entering the primary oxygen storage canister; and
catalyzing carbon monoxide molecules to form carbon dioxide molecules via the catalyst bed to create a flow of gases.

3. The process of claim 2, wherein concentrating the oxygen in a primary oxygen storage canister comprises:
measuring a level of carbon monoxide at an output of the catalyst bed;
allowing the flow of gases from the catalyst bed to the primary oxygen storage canister when the level of carbon monoxide at an output of the catalyst bed is below a carbon monoxide threshold; and
preventing the flow of gases from the catalyst bed to the primary oxygen storage canister and recirculating the flow of gases back to the catalyst bed when the level of carbon monoxide at the output of the catalyst bed is not below the carbon monoxide threshold.

4. The process of claim 3, wherein allowing a flow of gas from the catalyst bed to the primary oxygen storage canister further comprises:
absorbing, via rapid cycle amine cells, carbon dioxide from the flow of gases from the catalyst bed before the flow of gases enters the primary oxygen storage canister; and
venting the carbon dioxide.

5. The process of claim 4, wherein absorbing, via amine cells, carbon dioxide from the flow of gases from the catalyst bed comprises activating a first set of rapid cycle amine cells in opposite cycles of a second set of rapid cycle amine cells to stabilize heat transfer.

6. The process of claim 4 further comprising:
creating a pressure at the rapid cycle amine cells via a pressure swing pump; and
creating a vacuum at the rapid cycle amine cells via a vacuum swing pump.

7. The process of claim 2 further comprising:
absorbing carbon dioxide from the flow of gases via scrubbing media.

8. The process of claim 7, wherein concentrating the oxygen in a primary oxygen storage canister comprises:
measuring a level of carbon monoxide at an output of the scrubbing media;
allowing the flow of gases from the catalyst bed to the primary oxygen storage canister when the level of carbon monoxide at an output of the scrubbing media is below a carbon monoxide threshold; and
preventing the flow of gases from the scrubbing media to the primary oxygen storage canister and recirculating the flow of gases back to the scrubbing media when the level of carbon monoxide at the output of the scrubbing media is not below the carbon monoxide threshold.

9. The process of claim 7, absorbing carbon dioxide from the flow of gases via scrubbing media comprises absorbing carbon dioxide from the flow of gases via lithium hydroxide or calcium oxide.

10. The process of claim 2 further comprising:
absorbing carbon dioxide from the flow of gases via ionic liquid cells.

11. The process of claim 1, wherein removing the oxygen from the mixture of oxygen, carbon monoxide, and carbon dioxide is performed by an electrolytic sieve.

12. The process of claim 11 further comprising:
removing, before removing the oxygen from the mixture of oxygen, carbon monoxide, and carbon dioxide, contaminating gases that can poison or greatly reduce a viable operating time of the electrolytic sieve.

13. The process of claim 1, wherein:
removing the oxygen from the mixture of oxygen, carbon monoxide, and carbon dioxide comprises separating oxygen ions and combining the oxygen ions to form dioxygen molecules; and
concentrating the oxygen in a primary oxygen storage canister comprising storing the dioxygen molecules in the primary oxygen storage canister.

14. The process of claim 1 further comprising:
recycling exhaled oxygen from the breathing mask via a loop-back channel.

15. The process of claim 1 further comprising:
supplementing oxygen to the breathing mask from a second oxygen storage canister.

16. The process of claim 1 further comprising:
changing a flow rate of the process based on a variable flow pump.

17. The process of claim 1, further comprising:
measuring pressure of the breathing mask via a pressure sensor;
wherein metering the stored nitrogen and the stored oxygen to a user through a breathing mask at a habitable level of 19-21% oxygen is based on the pressure measured by the pressure sensor.

* * * * *